(12) United States Patent
Rivory et al.

(10) Patent No.: US 8,097,715 B2
(45) Date of Patent: Jan. 17, 2012

(54) MULTITARGETING INTERFERING RNAS HAVING TWO ACTIVE STRANDS AND METHODS FOR THEIR DESIGN AND USE

(75) Inventors: Laurent Pierre Rivory, New South Wales (AU); Michael Poidinger, New South Wales (AU); Donald John Birkett, New South Wales (AU); Gregory Martin Arndt, New South Wales (AU); Toby Passioura, New South Wales (AU)

(73) Assignee: Johnson & Johnson Research PTY Limited, Eveleigh, NSW (AU)

( * ) Notice: Subject to any disclaimer, the term of this patent is extended or adjusted under 35 U.S.C. 154(b) by 322 days.

(21) Appl. No.: 12/124,629

(22) Filed: May 21, 2008

(65) Prior Publication Data

US 2009/0192103 A1 Jul. 30, 2009

Related U.S. Application Data

(63) Continuation of application No. PCT/AU2006/001750, filed on Nov. 21, 2006.

(60) Provisional application No. 60/738,441, filed on Nov. 21, 2005, provisional application No. 60/738,640, filed on Nov. 21, 2005.

(51) Int. Cl.
*C07H 21/04* (2006.01)
*C07H 21/00* (2006.01)
*A61K 31/70* (2006.01)

(52) U.S. Cl. .......................... 536/24.5; 536/25.3; 514/44

(58) Field of Classification Search ....................... None
See application file for complete search history.

(56) References Cited

U.S. PATENT DOCUMENTS

| | | |
|---|---|---|
| 2005/0048529 A1 | 3/2005 | McSwiggen |
| 2005/0187174 A1 | 8/2005 | Richards et al. |
| 2005/0209180 A1* | 9/2005 | Jadhav et al. .................. 514/44 |

* cited by examiner

*Primary Examiner* — Tracy Vivlemore

(57) ABSTRACT

Interfering RNA molecules are now designed and produced with specificity for multiple binding sequences present in distinct genetic contexts in one or more pre-selected target RNA molecules and are used to modulate expression of the target sequences. The multitargeting interfering RNA molecules have two strands that target multiple target sites on one or more pre-selected RNA molecules. Such a multitargeting interfering RNA approach provides a powerful tool for gene regulation.

16 Claims, 3 Drawing Sheets

MULTITARGETING INTERFERING RNAS HAVING TWO ACTIVE STRANDS AND METHODS FOR THEIR DESIGN AND USE

CROSS-REFERENCE TO RELATED APPLICATIONS

This application is a continuation of PCT Application No. PCT/AU2006/001750 filed on Nov. 21, 2006, which claims priority to Provisional Application No. 60/738,441 filed Nov. 21, 2005 and 60/738,640 filed Nov. 21, 2005.

SEQUENCE LISTING

The instant application contains a Sequence Listing which has been submitted via EFS-Web and is hereby incorporated by reference in its entirety. Said ASCII copy, created on Apr. 21, 2010, is named 22238US3.txt and is 19,561 bytes in size.

FIELD OF THE INVENTION

The present invention concerns methods and reagents useful in modulating gene expression. Particularly, the invention relates to modulating gene expression using one multitargeting interfering RNA molecule having two strands each of which targets one or more sites on one or more pre-selected RNA molecules.

BACKGROUND OF THE INVENTION

It is now known that single and double-stranded RNA can modulate expression of or modify processing of target RNA molecules by a number of mechanisms. Some such mechanisms tolerate variation in the amount of sequence complementarity required between the modulatory (or interfering) RNA and the target RNA. Certain microRNAs can translationally repress target mRNA having as little as 6 nucleotides of complementarity with the microRNA. The development of RNA interference agents, for example, using double-stranded RNA to repress expression of disease-related genes is currently an area of intense research activity.

Double-stranded RNA of 19-23 bases in length is recognized by an RNA interference silencing complex (RISC) into which an effector strand (or "guide strand") of the RNA is loaded. This guide strand acts as a template for the recognition and destruction of highly complementary sequences present in the transcriptome. Alternatively, through the recognition and binding of RNA sequences of lower complementarity, interfering RNAs may induce translational repression without mRNA degradation. Such translational repression appears to be a mechanism of action of endogenous microRNAs, a group of short non-coding RNAs involved in differentiation and development.

Efforts at developing interfering RNAs for therapeutically applications thus far have focused on producing specific double-stranded RNAs, each with complete complementarity to a particular target transcript. Such double-stranded RNAs (dsRNAs) are potentially effective where a single suitable target can be identified. However, dsRNAs, particularly those designed against one target, may have at least two categories of off-target side effects that need to be avoided or minimized. Undesirable side effects can arise through the triggering of innate immune response pathways (e.g. Toll-like Receptors 3, 7, and 8, and the so-called interferon response) and through inadvertent inhibition of protein expression from related or unrelated transcripts (either by RNA degradation, translational repression or other mechanisms). Inadvertent side-effects can be obtained when the passenger strand of a duplex is loaded and generates suppression of RNA species distinct from those targeted by the putative guide strand. Loading bias is well understood and most design processes only select sequences for a RNAi duplex from which only the intended guide strand will be loaded. Thus, some bioinformatic and/or experimental approaches have been developed to try to minimize off-target effects. Algorithms for in silico hybridization are known, and others have been developed for predicting target accessibility and loading bias in an effort to eliminate or minimize side-effects while maintaining effectiveness.

Several double-stranded RNA molecules for potentially treating human diseases of viral and non-viral origin are in various stages of development. The diseases include Age-related Macular Degeneration, Amyotrophic Lateral Sclerosis (ALS), and Respiratory Syncytial Virus (RSV) infection. These RNA molecules, however, only target a single site in an RNA sequence. Although RNA interference may be useful and potent in obtaining knock-down of specific gene products, many diseases involve complex interactions between ontologically-unrelated gene products. Thus, the use of single-gene targeting approaches may not succeed except where a single or dominant pathophysiologic pathway can be identified and interrupted.

In fact, many putative targets can be identified for most diseases. Attempts to confirm that inhibiting single targets in isolation is therapeutically valuable have been disappointing. Indeed, obtaining therapeutic effectiveness is proving to be extremely challenging, probably because of multiple levels of redundancy in most signaling pathways. For example, many disorders, such as cancer, type 2 diabetes, and atherosclerosis, feature multiple biochemical abnormalities. In addition, some putative targets may be subject to enhanced mutation rates, thereby negating the effects of interfering RNAs on any such target.

For example, therapeutic approaches to viral infections continue to be major challenges in agriculture, as well as in animal and human health. The nature of the replication of viruses makes them highly plastic, "moving targets" therapeutically—capable of altering structure, infectivity, and host profile. The recent emergence of viruses such as Severe Acute Respiratory Syndrome ("SARS") and Avian Influenza Virus ("bird flu") exemplify these challenges. Even well-described viruses such as those involved in Acquired Immunodeficiency Syndrome or AIDS (e.g. Human Immunodeficiency Viruses, HIV-1 and HIV-2), continue to defy efforts at treatment and vaccination because of on-going viral mutation and evolution.

Furthermore, although nucleic acid therapeutics such as interfering RNAs are candidates for viral therapy, in part because modern rapid gene sequencing techniques allow viral genome sequences to be determined even before any encoded functions can be assessed, the error-prone replication of viruses, particularly RNA viruses, means that substantial genomic diversity can arise rapidly in an infected population. Thus far, strategies for the development of nucleic acid therapeutics have largely centered on the targeting of highly-conserved regions of the viral genome. It is unclear whether these constructs are efficient at treating viral infection or preventing emergence of resistant viral clones.

Therapeutic approaches that involve the design and use of one interfering RNA for control of several key "drivers" of the disease are thus desirable. Therefore, there is a need for interfering RNAs which can modulate multiple RNAs or target multiple sites within an RNA. Methods for the design and for making such therapeutic multi-targeting interfering RNAs are also needed. Antiviral interfering RNAs that can be developed rapidly upon the isolation and identification of new viral pathogens and that can be used to help slow, or even prevent, the emergence of new, resistant isotypes are also needed. Finally, it would be useful to have such RNAs wherein each of the two strands of a synthetic duplex independently targets at least one of the multiple target RNAs.

SUMMARY OF THE INVENTION

Interfering RNA molecules are now designed and produced with specificity for multiple binding sequences present in distinct genetic contexts in one or more pre-selected target RNA molecules and are used to modulate expression of the target sequences.

In a first embodiment, the present invention relates to a multitargeting interfering RNA molecule comprising Formula (I):

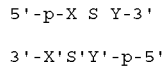

wherein p consists of a terminal phosphate group that is independently present or absent; wherein S consists of a first nucleotide sequence of a length of about 5 to about 20 nucleotides that is completely complementary to a first portion of a first binding sequence, and S' consists of a second nucleotide sequence of a length of about 5 to about 20 nucleotides that is completely complementary to a first portion of a second binding sequence, wherein said first and second binding sequences are present in distinct genetic contexts in at least one pre-selected target RNA molecule, and wherein S and S' are at least substantially complementary to each other but are not palindromic; and further wherein X, X', Y, or Y', is independently absent or consists of a nucleotide sequence; wherein XSY is at least partially complementary to the first binding sequence to allow stable interaction therewith; and wherein Y'S'X' is at least partially complementary to the second binding sequence to allow stable interaction therewith and is at least partially complementary to XSY to form a stable duplex therewith.

In one version of this preferred embodiment, X, X', Y, or Y', independently consists of one or more nucleotides and in another aspect of this embodiment X consists of a third nucleotide sequence that is at least partially complementary to a second portion of the first binding sequence, where the second portion is adjacent to and connected with the 3'-end of said first portion of the first binding sequence, and where X' consists of a fourth nucleotide sequence that is substantially complementary to the third nucleotide sequence. Preferably in this aspect X and X' are completely complementary to each other. It is also preferred that, X is completely complementary to the second portion of the first binding sequence.

In another aspect of this first embodiment, Y' is designed to consist of a fifth nucleotide sequence that is at least partially complementary to a second portion of the second binding sequence and the second portion is adjacent to and connected with the 3'-end of said first portion of the second binding sequence. In this aspect Y consists of a sixth nucleotide sequence that is substantially complementary to the fifth nucleotide sequence. Preferably Y and Y' are completely complementary to each other. It is also preferred that Y' is completely complementary to the second portion of the second binding sequence.

In yet other aspects of this first preferred embodiment, S and S' are completely complementary to each other. It is also preferred that XS is completely complementary to the first portion and the second portion of the first binding sequence. It is also contemplated that Y'S' is completely complementary to the first portion and the second portion of the second binding sequence. Further, XSY and Y'S'X' can be completely complementary to each other. Optionally, in aspects of this invention, S consists of a first nucleotide sequence of a length of about 8 to about 15 nucleotides and XSY and Y'S'X' preferably include lengths of about 15 to about 29 nucleotides. Also preferably, each of XSY and Y'S'X' are of a length of about 19 to about 23 nucleotides. In some aspects of this embodiment, the multitargeting interfering RNA molecule comprises one or more terminal overhangs and preferably these overhangs consists of 1 to 5 nucleotides. In other preferred aspects of this embodiment, the multitargeting interfering RNA molecule comprises at least one modified ribonucleotide, universal base, acyclic nucleotide, abasic nucleotide or non-ribonucleotide and more preferably, the multitargeting interfering RNA molecule comprises at least one 2'-O-methyl ribosyl substitution or a locked nucleic acid ribonucleotide.

In yet a further aspect of this first embodiment, the first and the second binding sequences of the multitargeting interfering RNA molecule are present in distinct genetic contexts in one pre-selected target RNA molecule or alternatively, the first and the second binding sequences are present in distinct genetic contexts in at least two pre-selected target RNA molecules. Preferably at least one of the pre-selected target RNA molecules is a non-coding RNA molecule. Also preferably, at least one of the pre-selected target RNA molecules is a messenger RNA (mRNA). In a further preferable embodiment at least one of the binding sequences is present in the 3'-untranslated region (3'UTR) of a mRNA molecule. Preferably the pre-selected target RNA molecules are involved in a disease or disorder of a biological system and the disease or disorder is preferably that of an animal or a plant. Preferred animals include, but are not limited to rat, a mouse, a dog, a cat, a pig, a monkey, and a human. Further the pre-selected target RNA molecules encode a protein of a class selected from the group consisting of receptors, cytokines, transcription factors, regulatory proteins, signaling proteins, cytoskeletal proteins, transporters, enzymes, hormones, and antigens. Preferred proteins include those selected from the group consisting of ICAM-1, VEGF-A, MCP-1, IL-8, VEGF-B, IGF-1, Gluc6p, Inpp11, bFGF, PlGF, VEGF-C, VEGF-D, β-catenin, κ-ras-B, κ-ras-A, EGFR, and TNF alpha and preferably the multitargeting interfering RNA molecule decreases expression of any combination of ICAM-1, VEGF-B, VEGF-C, VEGF-D, IL-8, bFGF, PlGF, MCP-1 and IGF-1 in an expression system. Also preferably the multitargeting interfering RNA molecule decreases expression of any combination of β-catenin, κ-ras, and EGFR in an expression system or decreases expression of both Gluc6p and Inpp11 in an expression system. Alternatively, the multitargeting interfering RNA targets viral RNA. Preferred viral targets include human immunodeficiency virus (HIV), a hepatitis C virus (HCV), an influenza virus, a rhinovirus, and a severe acute respiratory syndrome (SARS) virus. As one example, the multitargeting interfering RNA molecule targets hepatitis C virus (HCV) and an RNA molecule encoding TNFalpha.

In still further aspects of the present embodiment, one or more of the pre-selected target RNA molecules preferably comprises one or more RNA molecules selected from a first biological system. Alternatively, one or more of the pre-selected target RNA molecules comprises one or more RNA molecules selected from a second biological system that is infectious to a first biological system. In another aspect, the pre-selected target RNA molecules comprise one or more RNA molecules selected from a first biological system and one or more pre-selected target RNA molecules selected from a second biological system that is infectious to the first biological system. Preferably the pre-selected target RNA molecules comprise one or more RNA molecules selected from an animal or a plant and one or more RNA molecules selected from a microbe or a virus that is infectious to the animal or the plant. The pre-selected target RNA molecules preferably comprises an RNA molecule encoding a human protein TNFalpha, LEDGF(p75), BAF, CCR5, CXCR4, furin, NFkB, STAT1.

As examples of the multitargeting interfering RNA molecules of this invention, S preferably consists essentially of a nucleotide sequence selected from the group consisting of:

| | |
|---|---|
| GUGACAGUCACU, | (SEQ ID NO: 2) |
| CUGGGCGAGGCAG, | (SEQ ID NO: 21) |
| GUGGAUGUGGAG, | (SEQ ID NO: 22) |
| AGAAUCGCAAAACCAGC, | (SEQ ID NO: 34) |
| AGAAUCGCAAAACCA, | (SEQ ID NO: 36) |
| CAGGGGAGU, | (SEQ ID NO: 46) |
| AGGGCUCCAGGCG and | (SEQ ID NO: 63) |
| GCUGGCCGAGGAG. | (SEQ ID NO: 64). |

In further examples, S' consists essentially of a nucleotide sequence selected from the group consisting of:

| | |
|---|---|
| AGTGACTGTCAC, | (SEQ ID NO: 1) |
| CUGCCUCGCCCAG, | (SEQ ID NO: 19) |
| CUCCACAUCCAC, | (SEQ ID NO: 20) |
| GCTGGTTTTGCGATTCT, | (SEQ ID NO: 33) |
| TGGTTTTGCGATTCT, | (SEQ ID NO: 35) |
| ACTCCCCTG, | (SEQ ID NO: 41) |
| CGCCTGGAGCCCT and | (SEQ ID NO: 61) |
| CTCCTCGGCCAGC.. | (SEQ ID NO: 62) |

In yet other embodiments, the multitargeting interfering RNA molecules consist essentially of:

| | |
|---|---|
| 5'-CGAGUGACAGUCACUAGCUCC-3' | (SEQ ID NO: 3) |
| 3'-UAGCUCACUGUCAGUGAUCGA-5'; | (SEQ ID NO: 4) |
| 5'-UCGAGUGACAGUCACUAGCUC-3' | (SEQ ID NO: 7) |
| 3'-CUAGCUCACUGUCAGUGAUCG-5'; | (SEQ ID NO: 8) |
| 5'-UCGAGUGACAGUCACUAGCUCC-3' | (SEQ ID NO: 11) |
| 3'-CUAGCUCACUGUCAGUGAUCGA-5'; | (SEQ ID NO: 12) |
| 5'-CGAGUGACAGUCACUAGCUCC-3' | (SEQ ID NO: 3) |
| 3'-UAGUUCACUGUCAGUGAUCGA-5'; | (SEQ ID NO: 14) |
| 5'-UCGAGUGACAGUCACUAGUUC-3' | (SEQ ID NO: 15) |
| 3'-CUAGCUCACUGUCAGUGAUCG-5;' | (SEQ ID NO: 8) |
| 5'-CGAGUGACAGUCACUGAUUCC-3' | (SEQ ID NO: 16) |
| 3'-CUAGCCACUGUCAGUGAUCGA-5'; | (SEQ ID NO: 17) |
| 5'-GAUCGAGUGACAGUCACUAGCUC-3' | (SEQ ID NO: 65) |
| 3'-CUAGCUCACUGUCAGUGAUCG-5'; | (SEQ ID NO: 8) |
| 5'-CCUCACAGGGGAGUUGUGCCC-3' | (SEQ ID NO: 57) |
| 3'-UCGGAGUGUCCCCUCAACACG-5'; and | (SEQ ID NO: 58) |
| 5'-CCUCACAGGGGAGUUGUGCUU-3' | (SEQ ID NO: 59) |
| 3'-UUGGAGUGUCCCCUCAACACG-5' | (SEQ ID NO: 60) |

In another embodiment of the present invention the invention relates to a biological system comprising a multitargeting interfering RNA molecule comprising Formula (I):

$$5'\text{-}p\text{-}X\ S\ Y\text{-}3'$$
$$3'\text{-}X'S'Y'\text{-}p\text{-}5'$$

wherein p consists of a terminal phosphate group that is independently present or absent; wherein S consists of a first nucleotide sequence of a length of about 5 to about 20 nucleotides that is completely complementary to a first portion of a first binding sequence, and S' consists of a second nucleotide sequence of a length of about 5 to about 20 nucleotides that is completely complementary to a first portion of a second binding sequence, wherein said first and second binding sequences are present in distinct genetic contexts in at least one pre-selected target RNA molecule, and wherein S and S' are at least substantially complementary to each other but are not palindromic; and further wherein X, X', Y, or Y', is independently absent or consists of a nucleotide sequence; wherein XSY is at least partially complementary to the first binding sequence to allow stable interaction therewith; and wherein Y'S'X' is at least partially complementary to the second binding sequence to allow stable interaction therewith and is at least partially complementary to XSY to form a stable duplex therewith. In the present invention, preferred biological systems include virus, microbes, cells, plants, or animals.

The invention further relates to vectors comprising nucleotide sequences encoding the multitargeting interfering RNA molecules of this invention. Preferred vectors include viral vectors and preferred vectors are those selected from the group consisting of an adeno-associated virus, a retrovirus, an adenovirus, a lentivirus, and an alphavirus. Cells comprising these vectors are also contemplated in this invention. Where the multitargeting interfering RNA molecule is a short hairpin RNA molecule, vectors capable of encoding these short hairpin RNA molecule and those cells containing those vectors or the short hairpin RNA molecules of this invention are also contemplated.

The invention further relates to pharmaceutical compositions comprising the multitargeting interfering RNA molecules of this invention together with an acceptable carrier. Other pharmaceutical compositions include the vectors of this invention together with acceptable carriers.

In yet another embodiment of the present invention, the invention relates to a method of inducing RNA interference in a biological system, such as virus, microbes, cells, plants, or animals. These methods include the steps of introducing the multitargeting interfering RNA molecules of the present invention into those biological systems.

Further embodiments of this invention include methods for designing multitargeting interfering RNA molecule, comprising the steps of: a) selecting one or more target RNA molecules, wherein the modulation in expression of the target RNA molecules is desired; b) obtaining at least one nucleotide sequence for each of the target RNA molecules; c) selecting a length, n, in nucleotides, for a seed sequence, wherein n=about 6 or more; d) obtaining a collection of candidate seeds of the length n from each nucleotide sequence obtained in step b), wherein a candidate seed and its complete complement are not palindromic, and the candidate seed occurs at least once in one or more of the nucleotide sequences obtained in step b), and its complete complement occurs at least once in one or more of the nucleotide sequences obtained in step b); e) determining the genetic context of each of the candidate seeds and its complete complement, by collecting, for each occurrence of the candidate seed and its complete complement, a desired amount of the 5' and 3' flanking sequence; f) selecting a seed of the length n from the group of candidate seeds; g) selecting a first consensus target sequence, which comprises the seed and a consensus 3'-flanking sequence to the seed determined from the sequences obtained in step b); h) selecting a second consensus target sequence, which comprises the complete complement of the seed and a consensus 3'-flanking sequence to the complete complement of the seed determined from the sequences obtained in step b); i) obtaining a first strand sequence, which comprises the first consensus target sequence selected in step g) and, adjacent to and connected with the 5'-end of the first consensus target sequence, a complement of the consensus 3' flanking sequence of step h); j) obtaining a second strand sequence which comprises the second consensus target sequence selected in step h) and, adjacent to and connected with the 5'-end of the second consensus target sequence, a complement of the consensus 3' flanking sequence of step g), and; k) designing a multitargeting interfering RNA molecule comprising a first strand having the first strand sequence in step i) and a second strand having the second strand sequence obtained in step j).

In a preferred aspect of this embodiment, the invention further comprises the step of obtaining a collection of candidate seeds of the length n, the steps of: i) generating a first collection of sequences of the length n from each of the nucleotide sequences obtained in step b) above using a method comprising the steps of: 1) beginning at a terminus of each of the nucleotide sequence; 2) sequentially observing the nucleotide sequence using a window size of n; and 3) stepping along the nucleotide sequence with a step size of 1; ii) generating a second collection of sequences each of which is completely complementary to a sequence in the first collection; and iii) obtaining the collection of candidate seeds of the length n from the inspection of the first and the second collections of sequences, wherein a candidate seed and its complete complement are not palindromic, and each candidate seed and its complete complement occurs at least once in the nucleotide sequences obtained in step b) of the method provided above.

In another preferred aspect of this designing embodiment, the step of obtaining a collection of candidate seeds of the length n comprises the steps of: i) obtaining the completely complementary sequence for each nucleotide sequence obtained in step (b) of this designing method; ii) generating a first collection of sequences of the length n from each of the nucleotide sequences obtained in step b) and a second collection of sequences of the length n from each of the completely complementary sequences obtained in the present method, wherein the generating step comprises: 1) beginning at a terminus of the nucleotide sequence of each of the nucleotide sequences obtained in step b) above or each of the completely complementary sequences obtained in this aspect of the invention; 2) sequentially observing the nucleotide sequence using a window size of n; and 3) stepping along the nucleotide sequence with a step size of 1; and wherein following the generating step of this aspect the method further comprises iii) obtaining the collection of candidate seeds of the length n from the inspection of the first and the second collections of sequences, wherein a candidate seed and its complete complement are not palindromic, and each of the candidate seeds is present in both the first and the second collection of sequences.

In another preferred aspect of this embodiment, the step of selecting a group of candidate seeds comprises the step of discarding any sequence of the length n that: i) is composed of a consecutive string of 5 or more identical single nucleotides; ii) is composed of only adenosine and uracil; iii) is predicted to occur with unacceptable high frequency in the non-target transcriptome of interest; iv) is predicted to have a propensity to undesirably modulate the expression or activity of one or more cellular component; v) is any combination of i) to iv); or vi) is palindromic. Preferably, each of the steps of selecting a first and a second consensus target sequence comprises the step of discarding any sequence that; i) is composed of only a single base; ii) is composed of only adenosine and uracil; iii) has a consecutive string of five or more bases which are cytosine; iv) is predicted to occur with unacceptable high frequency in the non-target transcriptome of interest; v) is predicted to have a propensity to undesirably modulate the expression or activity of one or more cellular component; or vi) is any combination of i) to v).

The designing methods of this invention may further comprise the step of modifying the multitargeting interfering RNA molecule, i) to improve the incorporation of the first and the second strands of the multitargeting interfering RNA molecule into the RNA induced silencing complex (RISC); ii) to increase or decrease the modulation of the expression of at least one target RNA molecule; iii) to decrease stress or inflammatory response when the multitargeting interfering RNA molecule is administered into a subject; iv) to alter half life in an expression system; or v) any combination of i) to iv).

The designing methods of this invention preferably further comprise the steps of making the designed multitargeting interfering RNA molecule and testing it in a suitable expression system. Preferably the step of selecting a first consensus target sequence further comprises designing the consensus target sequence where the consensus 3' flanking sequence to the seed comprises a sequence that is at least partially identical to the 3' flanking sequence to the seed in at least one sequence obtained in step b) of the designing steps of this invention. Alternatively, the consensus 3'-flanking sequence to the seed can comprise a sequence that is identical to the 3' flanking sequence to the seed in at least one sequence obtained in step b) of the designing methods of this invention. Further, in the step of selecting a second consensus target sequence, in one aspect, the consensus 3' flanking sequence to the complete complement of the seed comprises a sequence that is at least partially identical to the 3' flanking sequence to the complete complement of the seed in at least one sequence obtained in step b). In other embodiments the consensus 3' flanking sequence to the complete complement of the seed comprises a sequence that is identical to the 3'-flanking sequence to the seed in the sequences obtained in step b). In yet other aspects related to this designing method, in the step of obtaining a first strand sequence, the complement of the consensus 3' flanking sequence is a complete complement of the consensus 3' flanking sequence of step h) of the designing method. Or, also preferably, in the step of obtaining a second strand sequence, the complement of the consensus 3' flanking sequence is a complete complement of the consensus 3' flanking sequence of step g). In a further aspect, in the step of designing a multitargeting interfering RNA molecule, the first strand and the second strand are completely complementary to each other, excepting the overhangs if present or in another aspect in the step of designing a multitargeting interfering RNA molecule, the first strand and the second strand are incompletely complementary to each other.

In another embodiment of this invention, the invention relates to a method of treating a subject, comprising the step of administering to said subject a therapeutically effective amount of a pharmaceutical composition comprising a multitargeting interfering RNA molecule of this invention. In a preferred aspect of this invention, the method further comprises administering to said subject a therapeutically effective amount of one or more additional therapeutic agents.

In yet another embodiment of this invention, the invention relates to a method of inhibiting the onset of a disease or condition in a subject, comprising administering to said subject a prophylactically effective amount of a pharmaceutical composition comprising at least one multitargeting interfering RNA molecule of this invention. Other embodiments include processes for making a pharmaceutical composition comprising mixing a multitargeting interfering RNA molecule of this invention and a pharmaceutically acceptable carrier.

Other aspects of the invention include methods of treating and methods of inhibiting the onset of a disease or disorder using a multitargeting interfering RNA of the invention, and methods of making a pharmaceutical composition comprising a multitargeting interfering RNA of the invention.

DETAILED DESCRIPTION OF THE DRAWINGS

Figure 1:
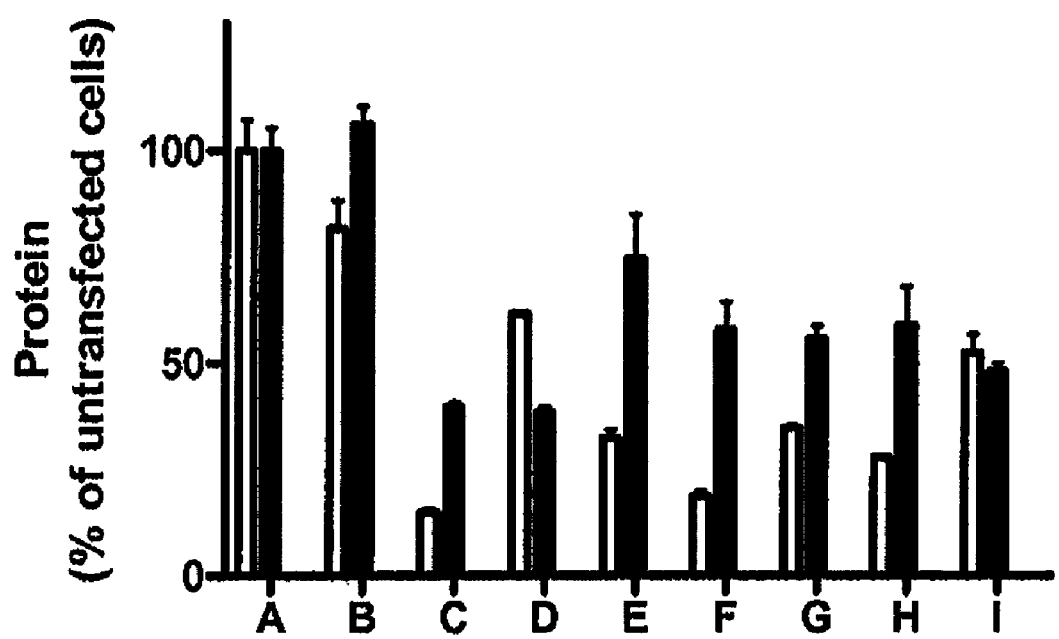
FIG. 1: Multitargeting of VEGF-A and ICAM-1 using both strands of a CODEMIR duplex. A 12 nt seed region was identified by analyzing the two target transcripts. Various permutations of positioning the CODEMIR around the seed were investigated and the resulting sequences are listed in Table 1-1. A: untransfected cells; B: irrelevant siRNA control; C: ICAM-1 and VEGF-specific siRNAs; D: CODEMIR-16; E: CODEMIR-17; F: CODEMIR-26; G: CODEMIR-27; H: CODEMIR-28 and I: CODEMIR-36. The activity of these CODEMIRs against ICAM-1 (open bars) and VEGF-A (closed bars) was determined using RPE cells. CODEMIR-27 and -28 correspond to the duplexes of CODEMIR-16 and -17, respectively, excepting the introduction of wobble basepairs into the extremities of the duplexes to adjust the loading bias. CODEMIR-36 is an example of an incompletely complementary duplex formed with guide strands that are fully complementary to the regions of VEGF-A and ICAM-1 mRNA targeted by CODEMIR16 and CODEMIR17.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. In this invention, certain terms are used frequently, which shall have the meanings as set forth as follows. These terms may also be explained in greater detail later in the specification.

The following are abbreviations that are at times used in this specification:
bp=base pair
cDNA=complementary DNA
CODEMIR=COmputationally-DEsigned, Multi-targeting Interfering RNAs
kb=kilobase; 1000 base pairs
kDa=kilodalton; 1000 dalton
miRNA=microRNA
ncRNA=non-coding RNA
nt=nucleotide
PAGE=polyacrylamide gel electrophoresis
PCR=polymerase chain reaction
RISC=RNA interference silencing complex
RNAi=RNA interference
SDS=sodium dodecyl sulfate
siRNA short interfering RNA
shRNA=short hairpin RNA
SNPs=single nucleotide polymorphisms
UTR=untranslated region
VIROMIR=multitargeting interfering RNA preferentially targeted to viral targets It must be noted that as used herein and in the appended claims, the singular forms "a," "an," and "the" include plural reference unless the context clearly dictates otherwise. Thus, for example, a reference to "a cell" is a reference to one or more cells and includes equivalents thereof known to those skilled in the art and so forth.

An "activity", a "biological activity", or a "functional activity" of a polypeptide or nucleic acid refers to an activity exerted by a polypeptide or nucleic acid molecule as determined in vivo or in vitro, according to standard techniques. Such activities can be a direct activity, such as the RNA interfering activity of an iRNA on a target RNA molecule, or an indirect activity, such as a cellular signaling activity mediated by the RNA interfering activity of an iRNA.

"Biological system" means, material, in a purified or unpurified form, from biological sources, including but not limited to human, animal, plant, insect, microbial, viral or other sources, wherein the system comprises the components required for biologic activity (e.g., inhibition of gene expression). The term "biological system" includes, for example, a cell, a virus, a microbe, an organism, an animal, or a plant.

A "cell" means an autonomous self-replicating unit that may constitute an organism (in the case of unicellular organisms) or is a sub unit of multicellular organisms in which individual cells may be specialized and/or differentiated for particular functions. A cell can be prokaryotic or eukaryotic, including bacterial cells such as E. coli, fungal cells such as yeast, bird cell, mammalian cells such as cell lines of human, bovine, porcine, monkey, sheep, apes, swine, dog, cat, and rodent origin, and insect cells such as Drosophila and silkworm derived cell lines, or plant cells. The cell can be of somatic or germ line origin, totipotent or hybrid, dividing or non-dividing. The cell can also be derived from or can comprise a gamete or embryo, a stem cell, or a fully differentiated cell. It is further understood that the term "cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

The term "complementary" or "complementarity" as used herein with respect to polynucleotides or oligonucleotides (which terms are used interchangeably herein) refers to a measure of the ability of individual strands of such poly- or oligonucleotides to associate with each other. Two major fundamental interactions in RNA are stacking and hydrogen bonding. Both contribute to free-energy changes for associations of oligoribonucleotides. The RNA-RNA interactions include the standard Watson-Crick pairing (A opposite U or T, and G opposite C) and the non-Watson-Crick pairing (including but not limited to the interaction through the Hoogsteen edge and/or sugar edge) (see e.g., Leontis et al., 2002, Nucleic Acids Research, 30: 3497-3531). A sequence that is complementary to another sequence is also referred to as the complement of the other.

The degree of complementarity between nucleic acid strands has significant effects on the efficiency and strength of the association between the nucleic acid strands.

"Complementarity" between two nucleic acid sequences corresponds to free-energy changes for helix formation. Thus, determination of binding free energies for nucleic acid molecules is useful for predicting the three-dimensional structures of RNAs and for interpreting RNA-RNA associations. e.g., RNAi activity or inhibition of gene expression or formation of double stranded oligonucleotides. Such determination can be made using methods known in the art (see, e.g., Turner et al., 1987, Cold Spring Harb Symp Quant Biol. 52:123-33; Frier et al., 1986, Proc. Nat. Acad. Sci. USA 83:9373-9377; Turner et al., 1987, J. Am. Chem. Soc. 109: 3783-3785).

As the skilled artisan will appreciate, complementarity, where present, can be partial, for example where at least one or more nucleic acid bases between strands can pair according to the canonical base pairing rules. For example, the sequences 5'-CTGACAATCG-3' (SEQ ID No:68), 5'-CGAAAGTCAG-3' (SEQ ID No:69) are partially complementary (also referred to herein as "incompletely complementary") to each other. "Partial complementarity" or "partially complementary" as used herein indicates that only a percentage of the contiguous residues of a nucleic acid sequence can form Watson-Crick base pairing with the same number of contiguous residues in a second nucleic acid sequence in an anti-parallel fashion. For example, 5, 6, 7, 8, 9, or 10 nucleotides out of a total of 10 nucleotides in the first oligonucleotide forming Watson-Crick base pairing with a second nucleic acid sequence having 10 nucleotides represents 50%, 60%, 70%, 80%, 90%, and 100% complementarity respectively.

Complementarity can also be total where each and every nucleic acid base of one strand is capable of forming hydrogen bonds according to the canonical base pairing rules, with a corresponding base in another, antiparallel strand. For example, the sequences 5'-CTGACAATCG-3' (SEQ ID No:68) and 5'-CGATTGTCAG-3' (SEQ ID No:70) are totally complementary (also referred to herein as "completely complementary") to each other. As used herein "complete complementarity" or "completely complementary" indicates that all the contiguous residues of a nucleic acid sequence can form Watson-Crick base pairing with the same number of contiguous residues in a second nucleic acid sequence in an anti-parallel fashion. A sequence that is completely complementary to another sequence is also referred to as the complete complement of the other.

The skilled artisan will appreciate that where there are no bases that can adequately base pair with corresponding contiguous residues in an antiparallel strand, the two strands would be considered to have no complementarity. In certain embodiments herein, at least portions of two antiparallel strands will have no complementarity. In certain embodiments such portions may comprise even a majority of the length of the two strands.

In addition to the foregoing, the skilled artisan will appreciate that in strands of equal length that are completely complementary, all sections of those strands are completely complementary to each other. Strands which are not of equal length, i.e. present in a nucleotide duplex having one or both ends not being blunt, may be considered by those of skill in the art to be completely complementary; however there will be one or more bases in the overhanging end or ends ("overhangs") which do not have corresponding bases in the opposing strand with which to base pair. In the case of strands that are incompletely or partially complementary, it is to be understood that there may be portions or sections of the strands wherein there are several or even many contiguous bases which are completely complementary to each other, and other portions of the incompletely complementary strands which have less than complete complementarity—i.e. those sections are only partially complementary to each other.

The percentage of complementarity between a first nucleotide sequence and a second nucleotide sequence can be evaluated by sequence identity or similarity between the first nucleotide sequence and the complement of the second nucleotide sequence. A nucleotide sequence that is X % complementary to a second nucleotide sequence is X % identical to the complement of the second nucleotide sequence. The "complement of a nucleotide sequence" is completely complementary to the nucleotide sequence, whose sequence is readily deducible from the nucleotide sequence using the rules of Watson-Crick base pairing.

"Conservation or conserved" indicates the extent to which a specific sequence is found to be represented in a group of related target sequences, regardless of the genetic context of the specific sequence.

"Genetic context" refers to the flanking sequences that surround a specific identified sequence and that are sufficiently long to enable one of average skill in the art to determine its position within a genome or RNA molecule relative to sequence annotations or other markers in common use.

"Sequence identity or similarity", as known in the art, is the relationship between two or more polypeptide sequences or two or more polynucleotide sequences, as determined by comparing the sequences. In the art, identity also means the degree of sequence relatedness between polypeptide or polynucleotide sequences, as the case can be, as determined by the match between strings of such sequences. To determine the percent identity or similarity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same or similar amino acid residue or nucleotide as the corresponding position in the second sequence, then the molecules are identical or similar at that position. The percent identity or similarity between the two sequences is a function of the number of identical or similar positions shared by the sequences (i.e., % identity=number of identical positions/total number of positions (e.g., overlapping positions)×100). Two sequences that share 100% sequence identity are identical. In one embodiment, the two sequences are the same length.

Both identity and similarity can be readily calculated. Methods commonly employed to determine identity or similarity between sequences include, but are not limited to those disclosed in Carillo et al, (1988), *SIAM J. Applied Math.* 48, 1073. Preferred methods to determine identity are designed to give the largest match between the sequences tested. Methods to determine identity and similarity are codified in computer programs.

A non-limiting example of a mathematical algorithm utilized for the comparison of two sequences is the algorithm of Karlin et al., (1990), *Proc. Natl. Acad. Sci. USA* 87:2264-2268, modified as in Karlin et al., (1993), *Proc. Natl. Acad. Sci. USA* 90:5873-5877. Such an algorithm is incorporated into the NBLAST and XBLAST programs of Altschul et al., (1990), *J Mol. Biol.* 215:403-410. To obtain gapped alignments for comparison purposes, Gapped BLAST can be utilized as described in Altschul et al., (1997), *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Additionally, the FASTA method (Atschul et al., (1990), *J. Molec. Biol.* 215, 403), can also be used.

Another non-limiting example of a mathematical algorithm useful for the comparison of sequences is the algorithm of Myers et al, (1988), *CABIOS* 4:11-17. Such an algorithm is incorporated into the ALIGN program (version 2.0).

In an embodiment, the percent identity between two sequences is determined using the Needleman and Wunsch (*J. Mol. Biol.* (48):444-453 (1970)) algorithm which has been incorporated into the GAP program in the GCG software package. The Accelrys GCG GAP program aligns two complete sequences to maximize the number of matches and minimizes the number of gaps.

In another embodiment, the percent identity between two sequences is determined using the local homology algorithm of Smith and Waterman (*J Mol Biol.* 1981, 147(1):195-7), which has been incorporated into the BestFit program in the Accelrys GCG software package. The BestFit program makes an optimal alignment of the best segment of similarity between two sequences. Optimal alignments are found by inserting gaps to maximize the number of matches.

Nucleotide sequences that share a substantial degree of complementarity will form stable interactions with each other, for example, by matching base pairs. As used herein, the term "stable interaction" with respect to two nucleotide sequences indicates that the two nucleotide sequences have sufficient complementarity and have the natural tendency to interact with each other to form a double stranded molecule. Two nucleotide sequences can form stable interaction with each other within a wide range of sequence complementarity. In general, the higher the complementarity the stronger or the more stable the interaction is. Different strengths of interactions may be required for different processes. For example, the strength of interaction for the purpose of forming a stable nucleotide sequence duplex in vitro may be different from that for the purpose of forming a stable interaction between an iRNA and a binding sequence in vivo. The strength of interaction can be readily determined experimentally or predicted with appropriate software by a person skilled in the art.

Hybridization can be used to test whether two polynucleotides are substantially complementary to each other and to measure how stable the interaction is. Polynucleotides that share a sufficient degree of complementarity will hybridize to each other under various hybridization conditions. In one embodiment, polynucleotides that share a high degree of complementarity thus form strong stable interactions and will hybridize to each other under stringent hybridization conditions. "Stringent hybridization conditions" has the meaning known in the art, as described in Sambrook et al., Molecular Cloning: A Laboratory Manual, Second Edition, Cold Spring Harbor Laboratory, Cold Spring Harbor, N.Y., (1989). An exemplary stringent hybridization condition comprises hybridization in 6× sodium chloride/sodium citrate (SSC) at about 45° C., followed by one or more washes in 0.2×SSC and 0.1% SDS at 50-65° C.

As used herein the term "mismatch" refers to a nucleotide of either strand of two interacting strands having no corresponding nucleotide on the corresponding strand or a nucleotide of either strand of two interacting strands having a corresponding nucleotide on the corresponding strand that is non-complementary.

As used herein, a "match" refers to a complementary pairing of nucleotides.

As used herein, the term "expression system" refers to any in vivo or in vitro system that can be used to evaluate the expression of a target RNA molecule and or the RNAi activity of a multitargeting RNA molecule of the invention. In particular embodiments, the "expression system" comprises one or more target RNA molecules, a multitargeting interfering RNA molecule targeting the target RNA molecules, and a cell or any type of in vitro expression system known to a person skilled in the art that allows expression of the target RNA molecules and RNAi.

As used herein, the term "RNA" includes any molecule comprising at least one ribonucleotide residue, including those possessing one or more natural nucleotides of the following bases: adenine, cytosine, guanine, and uracil; abbreviated A, C, G, and U, respectively, modified ribonucleotides, universal base, acyclic nucleotide, abasic nucleotide and non-ribonucleotides. "Ribonucleotide" means a nucleotide with a hydroxyl group at the 2' position of a p-D-ribofuranose moiety.

As used herein, the term "non-target transcriptome" or "non-targeted transcriptome" indicates the transcriptome aside from the targeted RNA molecules. For example, when a multitargeting interfering RNA is designed to target a viral RNA, the non-targeted transcriptome is that of the host. When a multitargeting interfering RNA is designed to target a given RNA in a biological system, the non-targeted transcriptome is the transcriptome of the biological system aside from the given targeted RNA.

Modified ribonucleotides include, for example 2'deoxy, 2'deoxy-2'-fluoro, 2'O-methyl, 2'O-methoxyethyl, 4'thio or locked nucleic acid (LNA) ribonucleotides. Also contemplated herein is the use of various types of ribonucleotide analogues, and RNA with internucleotide linkage (backbone) modifications. Modified internucleotide linkages include for example, phosphorothioate-modified, and even inverted linkages (i.e. 3'-3' or 5'-5'). Preferred ribonucleotide analogues include sugar-modified, and nucleobase-modified ribonucleotides, as well as combinations thereof. In preferred sugar-modified ribonucleotides the 2'—OH— group is replaced by a substituent selected from H, OR, R, halo, SH, SR, $NH_2$, NHR, $NR_2$ or ON, wherein R is C1-C6 alkyl, alkenyl or alkynyl and halo is F, Cl, Br, or I. In preferred backbone-modified ribonucleotides, the phosphoester group connecting to adjacent ribonucleotides is replaced by a modified group, e.g. a phosphorothioate group. Any or all of the above modifications may be combined. In addition, the 5'termini can be OH, phosphate, diphosphate or triphosphate. Nucleobase-modified ribonucleotides, i.e. ribonucleotides wherein the naturally-occurring nucleobase is replaced with a non-naturally occurring nucleobase instead, for example, uridines or cytidines modified at the S-position (e.g. 5-(2-amino)propyl uridine, and 5-bromo uridine); adenosines and guanosines modified at the 8-position (e.g. 8-bromo guanosine); deaza nucleotides (e.g. 7-deaza-adenosine); O- and N-alkylated nucleotides (e.g. N6-methyl adenosine) are also contemplated for use herein.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, Nucleic Acids Research, 29, 2437-2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

As used herein with respect to the listing of RNA sequences, the bases thymidine ("T") and uridine ("U") are frequently interchangeable depending on the source of the sequence information (DNA or RNA). Therefore, in disclosure of target sequences, seed sequences, candidate seeds, target RNA binding sites, and the like, the base "T" is fully interchangeable with the base "U". However, with respect to specific disclosures of the interfering RNA molecules of the invention, it is to be understood that for such sequences the use of the base "U" cannot be generally substituted with "T" in a functional manner. It is however known in the art that certain occurrences of the base "U" in RNA molecules can be substituted with "T" without substantially deleterious effect on functionality. For example, the substitution of T for U in overhangs, such as UU overhangs at the 3' end is known to be silent, or at a minimum, acceptable, and thus is permissible in the interfering RNA sequences provided herein. Thus, it is contemplated that the skilled artisan will appreciate how to vary even the specific interfering RNA sequences disclosed herein to arrive at other structurally-related and functionally-equivalent structures that are within the scope of the instant invention and the appended claims.

A "target RNA molecule" or a "pre-selected target RNA molecule" as used herein refers to any RNA molecule whose expression or activity is desired to be modulated, for example decreased, by an interfering RNA molecule of the invention in an expression system. A "target RNA molecule" can be a messenger RNA molecule (mRNA) that encodes a polypeptide of interest. A messenger RNA molecule typically includes a coding region and non-coding regions preceding ("5'UTR") and following ("3'UTR") the coding region. A "target RNA molecule" can also be a non-coding RNA (ncRNA), such as small temporal RNA (stRNA), micro RNA (miRNA), small nuclear RNA (snRNA), short interfering RNA (siRNA), small nucleolar RNA (snoRNA), ribosomal RNA (rRNA), transfer RNA (tRNA) and precursor RNAs thereof. Such non-coding RNAs can also serve as target RNA molecules because ncRNA is involved in functional or regulatory cellular processes. Aberrant ncRNA activity leading to disease can therefore be modulated by multitargeting interfering RNA molecules of the invention. The target RNA can further be the genome of a virus, for example a RNA virus, or a replicative intermediate of any virus at any stage, as well as any combination of these.

The "target RNA molecule" can be a RNA molecule that is endogenous to a biological system, or a RNA molecule that is exogenous to the biological system, such as a RNA molecule of a pathogen, for example a virus, which is present in a cell after infection thereof. A cell containing the target RNA can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

A "target RNA molecule" as used herein may include any variants or polymorphism of a desired RNA molecule. Most genes are polymorphic in that a low but nevertheless significant rate of sequence variability occurs in a gene among individuals of the same species. Thus, a RNA molecule may correlate with multiple sequence entries, each of which represents a variant or a polymorphism of the RNA molecule. In designing any gene suppression tool there is the risk that the selected binding sequence(s) used in the computer-based design may contain relatively infrequent alleles. As a result, the active sequence designed might be expected to provide the required benefit in only a small proportion of individuals. The frequency, nature and position of most variants (often referred to as single nucleotide polymorphisms (SNPs)) are easily accessible to those trained in the art. In this respect, sequences with a target molecule that are known to be highly polymorphic can be avoided in the selection of binding sequences during the bioinformatic screen. Alternatively, a limitless number of sequences available for any particular target may be used in the design stages of an interfering RNA of the invention to make sure that the targeted binding sequence is present in the majority of allelic variants, with the exception of the situation in which targeting of the allelic variant is desired (that is, when the allelic variant itself is implicated in the disease of interest).

A "target RNA molecule" comprises at least one targeted binding sequence that is sufficiently complementary to the guide sequence of an interfering RNA molecule of the invention to allow stable interaction of the binding sequence with the guide sequence. The targeted binding sequence can be refined to include any part of the transcript sequence (eg 5'UTR, ORF, 3'UTR) based on the desired effect. For example, translational repression is a frequent mechanism operating in the 3'UTR (i.e. as for microRNA). Thus, the targeted binding sequence can include sequences in the 3'UTR for effective translational repression.

The "targeted binding sequence", "binding sequence", or "target sequence" shall all mean a portion of a target RNA molecule sequence comprising a seed sequence and the sequence flanking either one or both ends of the seed, said binding sequence predicted to a form stable interaction with one strand of a multitargeting interfering RNA of the invention based on the complementarity between the said strand and the binding sequence.

As used herein the term "seed" or "seed sequence" or "seed region sequence" refers to a sequence of at least about 6 contiguous nucleotides present in a target RNA that is completely complementary to a portion of one strand of an interfering RNA. Although 6 or more contiguous bases are preferred, the expression "about 6" refers to the fact that windows of at least 5 or more contiguous bases or more can provide useful candidates in some cases and can ultimately lead to the design of useful interfering RNAs. Thus, all such seed sequences are contemplated within the scope of the instant invention.

As used herein, the term "interfering RNA" or "iRNA" is used to indicate single or double stranded RNA molecules that modulate the presence, processing, transcription, translation, or half-life of a target RNA molecule, for example by mediating RNA interference ("RNAi"), in a sequence-specific manner. As used herein, the term "RNA interference" or "RNAi" is meant to be equivalent to other terms used to describe sequence specific RNA interference, such as post-transcriptional gene silencing, translational inhibition, or epigenetics. This includes, for example, RISC-mediated degradation or translational repression, as well as transcriptional silencing, altered RNA editing, competition for binding to regulatory proteins, and alterations of mRNA splicing. It also encompasses degradation and/or inactivation of the target RNA by other processes known in the art, including but not limited to nonsense-mediated decay, and translocation to P bodies. Thus, the interfering RNAs provided herein (e.g. CODEMIRs and VIROMIRs) may exert their functional effect via any of the foregoing mechanisms alone, or in combination with one or more other means of RNA modulation known in the art. The interfering RNAs provided herein can be used to manipulate or alter the genotype or phenotype of an organism or cell, by intervening in cellular processes such as genetic imprinting, transcription, translation, or nucleic acid processing (e.g., transamination, methylation, etc.).

The term "interfering RNA" is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

The "interfering RNA" can be assembled from two separate oligonucleotides. The "interfering RNA" can also be assembled from a single oligonucleotide, comprising self-complementary regions linked by means of a nucleic acid based or non-nucleic acid-based linker(s). The "interfering RNA" can be a polynucleotide with a duplex, asymmetric duplex, hairpin or asymmetric hairpin secondary structure, having self-complementary regions. The "interfering RNA" can also be a single-stranded polynucleotide having one or more loop structures and a stem comprising self-complementary regions (e.g. short hairpin RNA, shRNA), wherein the polynucleotide can be processed either in vivo or in vitro to generate one or more double stranded interfering RNA molecules capable of mediating RNA inactivation. The cleavage of the self-paired region or regions of the single strand RNA to generate double-stranded RNA can occur in vitro or in vivo, both of which are contemplated for use herein.

As used herein, the "interfering RNA" need not be limited to those molecules containing only RNA, but further encompasses those possessing one or more modified ribonucleotides and non-nucleotides, such as those described supra.

The term "interfering RNA" includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the multitargeting interfering RNA or internally, for example at one or more nucleotides of the RNA.

Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally occurring RNA.

The interfering RNA of the invention, also termed "multi-targeting interfering RNA" is an interfering double-stranded RNA, each strand of which can form stable interactions with binding sites present in distinct genetic contexts on one or more target RNA molecules. Examples of the multitargeting interfering RNA include CODEMIRs, COmputationally-DEsigned, Multi-targeting Interfering RNAs, and VIROMIRs, where the latter multitargeting interfering RNA molecules are preferentially targeted to viral targets.

"Sequence" means the linear order in which monomers occur in a polymer, for example, the order of amino acids in a polypeptide or the order of nucleotides in a polynucleotide.

A "subject" as used herein, refers to an organism to which the nucleic acid molecules of the invention can be administered. A subject can be an animal or a plant, preferably a mammal, most preferably a human, who has been the object of treatment, observation or experiment, or any cell thereof.

A "vector" refers to a nucleic acid molecule capable of transporting another nucleic acid to which it has been linked. One type of vector is a "plasmid", which refers to a circular double stranded DNA loop into which additional DNA segments can be inserted. Another type of vector is a viral vector, wherein additional DNA segments can be inserted. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked.

As used herein, "modulate (or modulation of) the expression of an RNA molecule" means any RNA interference mediated regulation of the level and/or biological activity of the RNA molecule. It includes any RNAi-related post-transcriptional gene silencing, such as by cleaving, destabilizing the target RNA molecule or preventing their translation. In one embodiment, the term "modulate" can mean "inhibit," but the use of the word "modulate" is not limited to this definition. The modulation of the target RNA molecule is determined in a suitable expression system, for example in vivo, in one or more suitable cells, or in an acellular or in vitro expression system such as are known in the art. Routine methods for measuring parameters of the transcription, translation, or other aspects of expression relating to RNA molecules are known in the art, and any such measurements are suitable for use herein.

By "inhibit", "down-regulate", "reduce", or "decrease" or "decreasing" as with respect to a target RNA or its expression it is meant that the expression of the gene or level and/or biological activity of target RNA molecules is reduced below that observed in the absence of the nucleic acid molecules (e.g., multitargeting interfering RNA) of the invention. In one embodiment, inhibition, down-regulation or reduction with a multitargeting interfering RNA molecule is greater than that observed in the presence of an inactive or attenuated molecule. In another embodiment, inhibition, down-regulation, or reduction with a multitargeting interfering RNA molecule is greater than that observed in the presence of, for example, multitargeting interfering RNA molecule with scrambled sequence or with mismatches. In another embodiment, inhibition, down-regulation, or reduction of gene expression with a nucleic acid molecule of the instant invention is greater in the presence of the nucleic acid molecule than in its absence.

"Inhibit", "down-regulate", "reduce", or "decrease" as with respect to a target RNA or its expression encompasses, for example, reduction of the amount or rate of transcription or translation of a target RNA, reduction of the amount or rate of activity of the target RNA, and/or a combination of the foregoing in a selected expression system. The skilled artisan will appreciate that a decrease in the total amount of transcription, the rate of transcription, the total amount of translation, or the rate of translation, or even the activity of an encoded gene product are indicative of such a decrease. The "activity" of an RNA refers to any detectable effect the RNA may have in a cell or expression system, including for example, any effect on transcription, such as enhancing or suppressing transcription of itself or another RNA molecule. The measurement of a "decrease" in expression or the determination of the activity of a given RNA can be performed in vitro or in vivo, in any system known or developed for such purposes, or adaptable thereto. Preferably the measurement of a "decrease" in expression by a particular interfering RNA is made relative to a control, for example, in which no interfering RNA is used. In some comparative embodiments such measurement is made relative to a control in which some other interfering RNA or combination of interfering RNAs is used. Most preferably a change, such as the decrease is statistically significant based on a generally accepted test of statistical significance. However, because of the large number of possible measures and the need for the ability to rapidly screen candidate interfering RNAs, it is contemplated herein that a given RNA need only show an arithmetic decrease in one such in vitro or in vivo assay to be considered to show a "decrease in expression" as used herein.

More particularly, the biological modulating activity of the multitargeting interfering RNA is not limited to, or necessarily reliant on, degradation or translational repression by conventional RISC protein complexes involved in siRNA and microRNA gene-silencing, respectively. Indeed, short double-stranded and single-stranded RNA have been shown to have other possible sequence-specific roles via alternative mechanisms. For example, short double-stranded RNA (dsRNA) species may act as modulatory effectors of differentiation/cell activity, possibly through binding to regulatory proteins (Kuwabara, T., et al., (2004), *Cell,* 116: 779-93). Alternatively, dsRNA may lead to the degradation of mRNA through the involvement of AU-rich element (ARE)-binding proteins (Jing, Q., et al., (2005), *Cell,* 120: 623-34). Further, dsRNA may also induce epigenetic transcriptional silencing (Morris, K. V., et al., (2004) *Science,* 305: 1289-89). Processing of mRNA can also be altered through A to I editing and modified splicing.

As used herein, "palindrome" or "palindromic sequence" means a nucleic acid sequence that is completely complementary to a second nucleotide sequence that is identical to the nucleic acid sequence, e.g., UGGCCA. The term also includes a nucleic acid molecule comprising of two nucleotide sequences that are palindromic sequences.

"Phenotypic change" as used herein refers to any detectable change to a cell or an organism that occurs in response to contact or treatment with a nucleic acid molecule of the invention. Such detectable changes include, but are not limited to, changes in shape, size, proliferation, motility, protein expression or RNA expression or other physical or chemical changes as can be assayed by methods known in the art. The detectable change can also include expression of reporter genes/molecules such as Green Fluorescent Protein (GFP) or various tags that are used to identify an expressed protein or any other cellular component that can be assayed.

The term "therapeutically effective amount" as used herein, means that amount of active compound or pharmaceutical agent that elicits the biological or medicinal response in a tissue system, animal, human, or plant that is being sought by a researcher, veterinarian, medical doctor or other clinician, which includes ameliorating or alleviation of the symptoms of the disease or disorder being treated. Methods are known in the art for determining therapeutically effective doses for the instant pharmaceutical composition.

The term "prophylactically effective amount" refers to that amount of active compound or pharmaceutical agent that inhibits in a subject the onset of a disorder as being sought by a researcher, veterinarian, medical doctor or other clinician.

In general, the interfering RNAs known to one of ordinary skill in the art are double-stranded polynucleotide molecules comprising two self-complementary strands which are sense and antisense to the target. The iRNA duplex is usually designed such that the antisense (guide) strand is preferentially loaded into the RISC and guides the RISC-mediated degradation of the target nucleotide sequence following complementary base-pairing. The sense (passenger) strand may be degraded in the process of loading into the RISC complex or soon after by endonucleases to which single stranded RNA is highly sensitive. The relative thermodynamic characteristics of the 5' termini of the two strands of an interfering RNA determine whether a strand serves the function of a passenger or a guide strand during RNAi.

The present invention provides a multitargeting interfering RNA molecule comprising two strands, each of which is designed against a specific target sequence. The iRNA duplex is designed in such a manner that each strand can be loaded into RISC complexes and thus both strands function as "guide" strands. Preferably both strands are loaded to an approximately equal extent into RISC complexes. One strand is at least partially complementary to a first portion of a target RNA binding sequence, which is also referred to as the seed. The other strand comprises a sequence which is at least partially if not completely identical to the seed, this sequence being at least partially complementary to the first portion of a second target RNA binding sequence. The said first and second target binding sequences are present in distinct genetic contexts in at least one pre-selected target RNA molecule. That is, multiple target RNA binding sites may be present on the same target RNA molecule, on separate RNA molecules, or both.

In one general aspect, the present invention provides a multitargeting interfering RNA molecule comprising Formula (I):

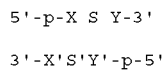

In Formula (I), p consists of a terminal phosphate group that can be present or absent from the 5'-end of either strand. Any terminal phosphate group known to a person skilled in the art can be used. Such phosphate group includes, but is not limited to, monophosphate, diphosphate, triphosphate, cyclic phosphate or to a chemical derivative of phosphate such as a phosphate ester linkage.

In Formula (I), S consists of a first nucleotide sequence of a length of about 5 to about 20 nucleotides that is completely complementary to a first portion of a first binding sequence, and S' consists of a second nucleotide sequence of a length of about 5 to about 20 nucleotides that is completely complementary to a first portion of a second binding sequence, wherein said first and second binding sequences are present in distinct genetic contexts in at least one pre-selected target RNA molecule, and wherein S and S' are at least substantially complementary to each other but are not palindromic.

In particular embodiments, S and S' each has a length of, for example, 5, 6, 7, 8, 9, 10, 11, 12, 13, 14, 15, 16, 17, 18, 19, or 20 nucleotides that are at least partially, preferably completely, complementary to the first portion of the at least two binding sequences. In one embodiment, S is completely complementary to a sequence present in one or more pre-selected target RNA molecules. In another embodiment, S' is completely complementary to a sequence present in one or more pre-selected target RNA molecules. In particular embodiments, S and S' are completely complementary to each other.

In certain embodiments, S is partially complementary to a first portion of a binding sequence present in one or more pre-selected target RNA molecules, such as 6 of 7, 7 of 8, 8 of 9, 9 of 10, 10 of 11, 11 of 12, 12 of 13, 13 of 14, 14 of 15, or 15 of 16 consecutive nucleotides of S are completely complementary to the first portion of at least one target RNA binding sequence. In other embodiments, S and the first portion of the distinct binding sequences have lesser overall complementarity such as 10 of 12, 11 of 13, 12 of 14, 13 of 15, or 14 of 16 nucleotides of complete complementarity. Similarly, in certain embodiments, S' is partially complementary to a first portion of a second binding site.

The remaining sequence of the two strands of the multitargeting interfering RNA (X, X', Y and Y') in Formula (I) is independently absent or consists of a nucleotide sequence. In particular embodiments, they are developed so as to generate further binding to the target RNA sites. In one embodiment, the sequences of X and Y' are at least partially complementary to the second portions of the first and second target RNA binding sequences, respectively. In one embodiment, the sequences X' and Y are completely complementary to X and Y', respectively, such that XSY and Y'S'X' are completely complementary. In an additional embodiment, X' and Y are incompletely complementary with X and Y', respectively such that XSY and Y'S'X' are incompletely complementary. This may be required, for example, in situations in which the loading bias of the interfering RNA duplex needs to be altered through the use of mismatches in the extremity with the higher hybridization energy.

In a further embodiment, the sequences X and Y' are designed so as to maximize binding of XS and Y'S' to the first and second portions of a plurality of target RNA binding sites. In this situation, the plurality of target sequences (e.g. viral isolates) can be examined in order to generate a number of identity consensus sequences corresponding to the second portion of the plurality of target RNA sequences. These identity consensus sequences can be generated by hand by examining the alignments of the target RNA sequences. Alternatively, all possible base sequences or a subset of putative XS and Y'S' sequences can be generated by computer algorithm. Each putative XS and Y'S' sequence is then hybridized in silico using RNAhybrid or a similar program known to one skilled in the art. Those putative sequences that are predicted to best bind the corresponding first and second portions of the target RNA binding sites are then prioritized for the next design phase, which includes filtering out putative sequences that have unfavorable characteristics such as more than 4 contiguous C or G bases.

In a preferred embodiment, the sequences of Y and X' are then designed such that they are at least partially complementary to Y' and X, respectively. Overhangs, if required may simply be the addition to X' and Y of UU, dTdT or any other base or modified base. In one embodiment, the bases of the overhangs are selected so as to further increase the predicted binding of XSY and Y'S'X' to their respective RNA targets. Overhangs may be 1, 2, 3, 4 or 5 bases as required.

In an interfering RNA of the invention, a preferred embodiment is one in which the two strands of the duplex independently have either partial or complete complementarity to their corresponding at least one target sequence and the two strands are completely complementary to one another, excepting the overhangs when present. Another embodiment of the invention is one in which each of the two strands of the duplex independently have either partial or complete complementary to their corresponding at least one target sequence and the two strands are incompletely complementary to one another. Both strands can be modified and refined to enhance some aspect of the function of the interfering RNA molecule of the invention. For example, various pharmacophores, dyes, markers, ligands, conjugates, antibodies, antigens, polymers, peptides and other molecules can be conveniently linked to the molecules of the invention. The interfering RNA can further comprise one or more 5' terminal phosphate group, such as a 5'-phosphate or 5',3'-diphosphate. These may be of use to improve cell uptake, stability, tissue targeting or any combination thereof.

In another embodiment, X consists of a nucleotide sequence that is at least partially complementary to a second portion of the first binding sequence, said second portion is adjacent to and connected with the 3'-end of said first portion of the first binding sequence, and wherein X' is substantially complementary to X. In a particular embodiment, X and X' are completely complementary to each other. In another particular embodiment, X is completely complementary to the second portion of the first binding sequence.

In yet another embodiment, Y' consists of a nucleotide sequence that is at least partially complementary to a second portion of the second binding sequence, said second portion is adjacent to and connected with the 3'-end of said first portion of the second binding sequence, and wherein Y is substantially complementary to Y'. In a particular embodiment, Y and Y' are completely complementary to each other. In another particular embodiment, Y' is completely complementary to the second portion of the second binding sequence.

In Formula (I), XSY is at least partially complementary to the first binding sequence to allow stable interaction of XSY with the first binding sequence, and Y'S'X' is at least partially complementary to the second binding sequence to allow stable interaction with the second binding sequence, and XSY and Y'S'X' are at least partially complementary to each other to allow formation of a stable iRNA duplex. In a particular embodiment, XSY is completely complementary to the first binding sequence. In another embodiment, Y'S'X' is completely complementary to the second binding sequence. In yet another embodiment, XSY and Y'S'X' are completely complementary to each other.

In an embodiment of the present invention, each strand of a multitargeting interfering RNA molecule of the invention is independently about 17 to about 25 nucleotides in length, in specific embodiments about 17, 18, 19, 20, 21, 22, 23, 24, and 25 nucleotides in length. Using shorter length interfering RNA molecules without the need for the generation of multiple active sequences through processing of RNA by enzymes such as Dicer and RNaseIII, provides advantages, for example, in reduction of cost, manufacturing, and chance of off-target effects.

The interaction between the two strands can be adjusted to improve loading of both strands into the cellular RISC complex (Khvorova et al. (2003) Cell, 115: 209-16; Schwarz et al. (2003) Cell, 115: 199-208), or to otherwise improve the functional aspects of the interfering RNA. The skilled artisan will appreciate that there are routine methods for altering the strength and other properties of the base paired strands through the addition, deletion, or substitution of one or more bases in either strand of the synthetic duplex. In particular as one example, these strategies can be applied to the design of the extremities of the duplex to ensure that the predicted thermodynamics of the duplex are conducive to the loading of the desired strand. These strategies are well known to persons skilled in the art.

It is also contemplated herein that a single-stranded RNA molecule comprises, for example, a hairpin loop or similar secondary structure that allows the molecule to self-pair to form at least a region of double-stranded nucleic acid of Formula (I).

The skilled artisan will appreciate that the double-stranded RNA molecules provide certain advantages for use in therapeutic applications. Although blunt-ended molecules are disclosed herein for certain embodiments, in various other embodiments, overhangs, for example of 1-5 nucleotides, are present at either or both termini. In some embodiments, the overhangs are 2 or 3 bases in length. Presently preferred overhangs include 3'-terminus UU overhangs (3'-UU) in certain embodiments. Other overhangs exemplified for use herein include, but are not limited to, 3'-AA, 3'-CA, 3'-AU, 3'-UC, 3'-CU, 3'-UG, 3'-CC, 3'-UA, 3'-U, and 3'-A. Still other either 5'-, or more preferably 3'-, overhangs of various lengths and compositions are contemplated for use herein on the RNA molecules provided.

In certain embodiments, the multitargeting interfering RNA molecule of the invention comprises one or more terminal overhangs, for example, an overhang consisting 1 to 5 nucleotides. In other embodiments, the multitargeting interfering RNA molecule of the invention comprises at least one modified ribonucleotide, such as one 2'-O-methyl ribosyl substitution.

In certain embodiments at least one target RNA molecule is an mRNA. More specifically, in some embodiments at least one target encodes a receptor, cytokine, transcription factor, regulatory protein, signaling protein, cytoskeletal protein, transporter, enzyme, hormone, or antigen. As such, the potential range of protein targets in the cell is not limited, however the skilled artisan will appreciate that certain targets are more likely to be of value in a particular disease state or process. In addition, the skilled artisan will appreciate that target RNA molecules, whether coding or regulatory, originating from a pathogen (e.g. a virus) are useful with the multitargeting interfering RNAs and methods provided herein.

In one embodiment, at least one of the binding sequences is in the 3'UTR of an mRNA.

The inclusion of one target or more targets does not preclude the use of, or intention for, a particular interfering RNA to target another selected target. Such targeting of any additional RNA target molecules may result in less, equal, or greater effect in an expression system.

Notwithstanding the foregoing, the multitargeting interfering RNAs of the instant invention are preferably screened for off-target effects, especially those that are likely. For example, reviewing the potential binding to the entire transcriptome, or as much of it as is known at the time provides a useful approach to such screening. For example, where a genome has been completely sequenced, the skilled artisan will appreciate that the entire transcriptome can be conveniently screened for likely off-target effects. In cases for which local delivery of multitargeting interfering RNA is anticipated, specialized tissue-specific transcriptomes (eg retina for ocular applications) may be more relevant because non-target transcripts that are identified through bioinformatic approaches from the complete transcriptome may actually not be present in the tissue into which the multitargeting interfering RNA is applied.

In one embodiment, the two strands of a multitargeting interfering RNA of the invention form stable interaction with at least two distinct targeted binding sequences present in distinct genetic contexts on a single target RNA molecule, and thus modulates the expression or activity of the RNA molecule. Targeting multiple binding sites on a single target RNA molecule with a single iRNA provides more effective RNAi of the target RNA molecule. This approach is particularly useful for the modulation of virus gene expression where the mutation rate is high.

In another embodiment, the two strands of a multitargeting interfering RNA of the invention form stable interaction with at least two binding sequences present in distinct genetic contexts on multiple pre-selected target RNA molecules, and thus modulates the expression or activity of multiple pre-selected target RNA molecules. Targeting multiple target RNA molecules with a single iRNA represents an alternative to the prototypical one drug one target approach. In considering the complexity of biological systems, designing a drug selective for multiple targets will lead to new and more effective medications for a variety of diseases and disorders.

In specific embodiments, RNA molecules that are involved in a disease or disorder of a biological system are pre-selected and targeted by a multitargeting interfering RNA molecule of the invention. The biological system can be, for example, a plant, or an animal such as a rat, a mouse, a dog, a pig, a monkey, and a human. The pre-selected target RNA molecules can, for example, encode a protein of a class selected from the group consisting of receptors, cytokines, transcription factors, regulatory proteins, signaling proteins, cytoskeletal proteins, transporters, enzymes, hormones, and antigens. The pre-selected target RNA molecules can, for example, encode a protein selected from the group consisting of ICAM-1, VEGF-A, MCP-1, IL-8, VEGF-B, IGF-1, Gluc6p, Inppl1, bFGF, PlGF, VEGF-C, VEGF-D, β-catenin, κ-ras-B, κ-ras-A, EGFR, and TNF alpha. Therefore, the multitargeting interfering RNA molecule of the invention can, for example, modulate expression of any combination of ICAM-1, VEGF-B, VEGF-C, VEGF-D, IL-8, bFGF, PlGF, MCP-1 and IGF-1, any combination of ICAM-1, VEGF-A and IGF-1, any combination of β-catenin, κ-ras, and EGFR, both ICAM-1 and VEGF-A, or both Gluc6p and Inppl1, in a biological system, such as an animal.

The pre-selected target RNA molecule can also be a viral RNA, including a viral RNA encoding a protein essential for the virus. Such essential proteins can, for example, be involved in the replication, transcription, translation, or packaging activity of the virus. Exemplary essential proteins for a HIV virus are GAG, POL, VIF, VPR, TAT, NEF, REV, VPU and ENV, all of which can be a pre-selected target molecule of the invention. The multitargeting interfering RNA of the invention can be used to modulate viral RNA from, including but not limited to, a human immunodeficiency virus (HIV), a hepatitis C virus (HCV), an influenza virus, a rhinovirus, and a severe acute respiratory syndrome (SARS) virus or a combination thereof.

In some embodiments, the multitargeting interfering RNA of the invention are designed to target one or more target RNA molecules in a first biological system and one or more target molecules in a second biological system that is infectious to the first biological system. In particular embodiments, the multitargeting interfering RNA of the invention are designed to target one or more host RNA molecules and one or more RNA molecules of a virus or a pathogen for the host. In particular embodiments of the invention, the viral RNA is HCV or HIV and the host target RNA includes, but is not limited to, TNFalpha, LEDGF(p75), BAF, CCR5, CXCR4, furin, NFkB or STAT1.

In particular embodiments of the invention, specific multitargeting interfering RNA molecules are provided in the Examples that are functional against specific targets. These CODEMIRs and/or VIROMIRs are useful for decreasing expression of RNAs, for example, their intended target RNA molecules and data supporting the activity are also provided herein in the working examples. Such molecules, the skilled artisan will appreciate, can target multiple sites on a single RNA or multiple sites on two or more RNAs and are useful to decrease the expression of such one or preferably two or more such targeted RNAs in an expression system.

Other active CODEMIRs were found including PF018 which targets the seed of GUUGUGGAA (SEQ ID NO: 91) in IL-8 and MCP-1. This CODEMIR, with the guide sequence UUCCACAACACAAGCUGUGUU (SEQ ID NO: 135), suppressed IL-8 and MCP-1 secretion by 45% and 60%, respectively. The CODEMIR PF018 duplex is as follows:

5'-UUCCACAACACAAGCUGUGUU-3' (SEQ ID NO: 135) (guide strand)
3'-UUAAGGUGUUGUGUUCGACAC-5' (SEQ ID NO: 136) (passenger strand)

In some embodiments, a given multitargeting interfering RNA will be more effective at modulating expression of one of several target RNAs than another. In other cases, the multitargeting interfering RNA will similarly affect all targets in one or more expression systems. Various factors can be responsible for causing variations in silencing or RNAi efficiency: (i) asymmetry of assembly of the RISC causing one strand to enter more efficiently into the RISC than the other strand; (ii) inaccessibility of the targeted segment on the target RNA molecule; (iii) a high degree of off-target activity by the interfering RNA; (iv) sequence-dependent variations for natural processing of RNA, and (v) the balance of the structural and kinetic effects described in (i) to (iv). See Hossbach et al. (2006), *RNA Biology* 3: 82-89. In designing a multitargeting interfering RNA molecule of the invention, special attention can be given to each of the listed factors to increase or decrease the RNAi efficiency on a given target RNA molecule.

Another general aspect of the invention is a method for designing a multitargeting interfering RNA. The method of the invention includes various means leading to a multitargeting interfering RNA that effectively target distinct binding sequences present in distinct genetic contexts in one or more pre-selected target RNA molecules. In one embodiment, a multitargeting interfering RNA can be designed by visual or computational inspection of the sequences of the target molecules, for example, by comparing target sequences and their complements and identifying sequences of length n which occur in both the target sequence and the complement of the target sequence sets. In another embodiment, a multitargeting interfering RNA can be designed by visual or computational inspection of the sequences of the target molecules to find occurrences of the sequence of length n and of its complete complement within the set of target sequences. Alternatively, all possible sequences of a pre-selected length n can be generated by virtue of each permutation possible for each nucleotide position to a given length ($4^n$) and then examining for their occurrence in the pre-selected nucleotide sequences and their complements. Alternatively, all possible sequences of a pre-selected length n and their complete complements can be generated by virtue of each permutation possible for each nucleotide position to a given length ($4^n$) and then examining for their occurrence in the pre-selected nucleotide sequences.

In one embodiment, when there is a plurality of target sequences, a multitargeting interfering RNA can be designed by visual or computational inspection of the sequences of the target molecules, for example, by aligning sequences and visually or computationally finding consensus target sequences for the design.

For both strands of a given multitargeting interfering RNA molecule of the invention to be active, the rational design process requires that each strand be capable of modulating expression of its intended target (i.e. each strand is "active" against its target RNA, e.g. by having at least partial complementarity thereto) while simultaneously requiring that each of the strands is at least sufficiently complementary to the other that a duplex can form. In essence there is no strand which is solely a guide strand or solely a passenger strand because each strand serves as both guide strand and passenger strand. The skilled artisan will also appreciate that such molecules can be designed as single strands with hairpin structures that can, for example, be processed in vivo to become a duplex consisting of two separate strands.

In an embodiment, the invention provides a method for designing a multitargeting interfering RNA molecule, comprising the steps of:
  a) selecting one or more target RNA molecules, wherein the modulation in expression of the target RNA molecules is desired;
  b) obtaining at least one nucleotide sequence for each of the target RNA molecules;
  c) selecting a length, n, in nucleotides, for a seed sequence, wherein n=about 6 or more;
  d) obtaining a collection of candidate seeds of the length n from each nucleotide sequence obtained in step b), wherein a candidate seed and its complete complement are not palindromic, and the candidate seed occurs at least once in one or more of the nucleotide sequences obtained in step b), and its complete complement occurs at least once in one or more of the nucleotide sequences obtained in step b);
  e) determining the genetic context of each of the candidate seed and its complete complement, by collecting, for each occurrence of the candidate seed and its complete complement, a desired amount of the flanking sequences;

f) selecting a seed of the length n from the group of candidate seeds;

g) selecting a first consensus target sequence, which comprises the seed and a consensus 3'-flanking sequence to the seed determined from the sequences obtained in step b);

h) selecting a second consensus target sequence, which comprises the complete complement of the seed and a consensus 3' flanking sequence to the complete complement of the seed determined from the sequences obtained in step b);

i) obtaining a first strand sequence, which comprises the first consensus target sequence selected in step g) and, adjacent to and connected with the 5'-end of the first consensus target sequence, a complement of the consensus 3' flanking sequence of step h);

j) obtaining a second strand sequence which comprises the second consensus target sequence selected in step h) and, adjacent to and connected with the 5'-end of the second consensus target sequence, a complement of the consensus 3' flanking sequence of step g), and;

k) designing a multitargeting interfering RNA molecule comprising a first strand having the first strand sequence in step i) and a second strand having the second strand sequence obtained in step j).

The method further comprise repeating steps g) to k) for each seed of length n selected from the group of candidate seeds in step f).

The method further comprises the step of repeating steps c) to k) for another desired seed length. In one embodiment, the first scan through target sequences will begin with any seed length (e.g. n=9) and subsequent rounds of searching will either increase or decrease the seed length (e.g. based on the number of seeds returned in previous scans). A person of ordinary skill in the art will recognize that the number of candidate seeds will increase as the length of the seed is decreased.

One skilled in the art will realize that finding a candidate seed present in at least one of the selected RNA sequences and in at least one complement of the selected RNA sequences, is an alternative to finding the candidate seed and its complete complement in the selected RNA sequences.

One skilled in the art will recognize that these design steps may be performed in a different order to produce an equivalent final product. Also, one skilled in the art will recognize that some steps can be substituted with alternative procedures that are broadly equivalent as shown in the Examples. One skilled in the art will appreciate that the six elements of Formula I (X, S, Y, X', S', Y') can be determined and assembled in a number of ways.

Often the preference for designing a multitargeting interfering RNA molecule of the invention involves: firstly, identifying the seed and its complement, which occur in different genetic contexts; secondly, determining XS and Y'S' so as to bind to their respective target RNA sequences, and then determining XSY and Y'S'X' wherein Y is the complement of Y' and X' is the complement of X. As an example, XS may be determined as the complement of the seed (equates to S) together with the complement of a portion of the 3' flanking sequence of the seed (equates to X). Similarly, Y'S' may be determined as the complement of the complement of the seed (equates to S') together with the complement of a portion of the 3' flanking sequence of the complement of the seed (equates to Y'). In cases in which it is desired to target a plurality of sequences, the plurality of 3' flanking sequences may be examined to yield consensus 3' flanking sequences. X and/or Y' can then be determined as the complements of these consensus 3' flanking sequences. Further modifications can be made to the molecule as described in this specification.

Preferred target RNA molecules are strategically selected molecules, for example viral or host RNAs involved in disease processes, viral genomes, particularly those of clinical significance, and the like. A detailed discussion of target RNA is provided above and applies equally to this and other aspects of the invention, as if set out in its entirety here. The basis for the selection of a target RNA molecule will be appreciated by those of skill in the art. Preferred target RNAs are those involved in diseases or disorders one wishes to control by the administration of the multitargeting interfering RNA.

The step of obtaining the sequences for the selected target is conducted by obtaining sequences from publicly available sources, such as the databases provided by the National Center For Biotechnology Information (NCBI) (through the National Institutes of Health (NIH) in the United States), the European Molecular Biology Laboratories (through the European Bioinformatics Institute throughout Europe) available on the World-Wide Web, or proprietary sources such as fee-based databases and the like. Sequences can also be obtained by direct determination. This may be desirable where a clinical isolate or an unknown gene is involved or of interest, for example, in a disease process. Either complete or incomplete sequences of a target RNA molecule can be used for the design of multitargeting interfering RNA of the invention.

Also provided herein are methods wherein a plurality of independent target nucleotide sequences are obtained in step b) for each of one or more target RNA molecules selected in step a). The databases described above frequently have multiple sequences available for particular targets. This is especially true where genetic variation is naturally higher, for example with viral sequences. In various embodiments, the plurality of target nucleotide sequences represents strain variation, allelic variation, mutation, or multiple species. The number of such a plurality of sequences may range from several or a low multiple, to numerous—for example dozens or even hundreds or thousands of sequences for a given target. It is especially possible to have such numbers of sequences when working with viral sequences.

The sequences chosen can be further limited based on additional desirable or undesirable features such as areas of low sequence complexity, poor sequence quality, or those that contain artifacts relating to cloning or sequencing such as inclusion of vector-related sequences. Furthermore, regions with extensive inaccessible secondary structure could be filtered out at this stage. Indeed, Luo and Chang have demonstrated that siRNA targeting accessible regions of mRNA structure such as loops were more likely to be effective than those aligned with stems (Luo & Chang, (2004), *Biochem. Biophys. Res. Commun.*, 318: 303-10). The sequences chosen, however, need not be limited to 3'UTR sequences or regions of low secondary structure.

The step of selecting a length of n nucleotide bases for a seed sequence is preferably an iterative process that does not require any particular basis or logic at first glance—i.e. the starting seed length may be any number of bases above about 6. The longer the length that is chosen for a seed, the less likely that it and its complete complement will appear in the at least one target RNA, e.g. in a target RNA sequence. The shorter the seed sequence length, the more frequently it will occur as would be expected. Preferably, an iterative process is used to find the preferred sequences for candidate seeds as described below. Thus, after a particular value for n is used to identify candidate seeds of length n, another value (e.g. n+1, n−1) will be used and the process can be repeated to identify candidate seed sequences of length n+1, n−1 and so on.

The seeds are selected from a pool of "candidate seeds," also referred to herein as "seed candidates." Seed candidates include sequences of a particularly desired or selected length each of which and its complete complement are not palindromic, and wherein the candidate seed occurs at least once in one or more of the nucleotide sequences obtained in step b), and its complete complement occurs at least once in one or more of the nucleotide sequences obtained in step b). The candidate seeds are preferably generated by computer, for example by moving stepwise along a target sequence with a "window" (expressed in terms of a fixed number of contiguous nucleotides) of the desired or selected seed length. Preferably each step is a single base progression, thus generating a "moving window" of selected length through which each target sequence is sequentially viewed. Other step distances are contemplated, however, the skilled artisan will appreciate that only a step of one nucleotide will allow the generation of all possible seeds sequences.

Particularly, a collection of candidate seeds of the length n can be obtained by the steps of:
  i) generating a first collection of sequences of the length n from each of the nucleotide sequences chosen for the target molecules, using a method comprising the steps of:
    1) beginning at a terminus of each of the nucleotide sequence;
    2) sequentially observing the nucleotide sequence using a window size of n; and
    3) stepping along the nucleotide sequence with a step size of 1;
  ii) generating a second collection of sequences each of which is completely complementary to a sequence in the first collection; and
  iii) obtaining the collection of candidate seeds of the length n from the inspection of the first and the second collections of sequences, wherein a candidate seed and its complete complement are not palindromic, and each of the candidate seed and its complete complement each occurs at least once in the nucleotide sequences for the target molecules.

In another embodiment, a collection of candidate seeds of the length n can be obtained by the steps of:
  i) obtaining the completely complementary sequence for each nucleotide sequence chosen for the target molecules;
  ii) generating a first collection of sequences of the length n from each of the nucleotide sequences chosen for the target molecules and a second collection of sequences of the length n from each of the completely complementary sequences obtained in step (i), using a method comprising the steps of:
    1) beginning at a terminus of the nucleotide sequence of each of the nucleotide sequences chosen for the target molecules or each of the completely complementary sequences obtained in step (i);
    2) sequentially observing the nucleotide sequence using a window size of n; and
    3) stepping along the nucleotide sequence with a step size of 1; and
  iii) obtaining the collection of candidate seeds of the length n from the inspection of the first and the second collections of sequences, wherein a candidate seed and its complete complement are not palindromic, and each of the candidate seeds is present in both the first and the second collections of sequences.

In one embodiment, the method further comprises the step of discarding candidate seed sequences for which either the seed or its complete complement do not occur with at least a predetermined minimum frequency in the target nucleotide sequences.

Preferably the method ultimately chosen will include one or more of these steps, or all of them as needed. For example, in one embodiment, the method further comprises the step of discarding any candidate seed sequence that: is composed of only a single base, is composed only of A and U, has a consecutive string of 5 or more C or 5 or more G, is predicted to occur with unacceptable frequency in the non-target transcriptome of interest; is predicted to have a propensity to undesirably modulate the expression or activity of one or more cellular component (eg. to undesirably activate a cellular sensor of foreign nucleic acid), or any combination thereof.

Seeds then are selected from the pool of candidate sequences as the ones where the seed is present in one genetic context, and its complete complement is present in a different genetic context in the at least one pre-selected target sequence. Genetic contexts are determined by collecting, for each occurrence of the candidate seed sequence, a desired amount of the 5' and 3' flanking sequence. The genetic context of the complement of the seed is determined in a similar fashion.

In an exemplary process of making a multitargeting interfering RNA of the invention when one or both strands are each required to target a plurality of RNA sequences (e.g. multiple viral isolates), a "consensus target sequence" is selected for one or both strands of the interfering RNA.

The term "consensus target sequence" does not suggest that there is only one best sequence approximating multiple binding sequences on target molecule(s), rather a population of one or more alternative sequences may all be consensus target sequences.

A first consensus target sequence for the first strand of the iRNA comprises a seed sequence and a consensus 3'-flanking sequence to the seed in at least one of the chosen sequences for the target molecules. A second consensus target sequence for the second strand of the iRNA comprises the complete complement of the seed and a consensus 3' flanking sequence to the complete complement of the seed in at least one of the chosen sequences for the target molecules.

The "consensus 3' flanking sequence" of the seed is readily derived by visual inspection, or through the use of bioinformatic tools or calculations, from the examination of the genetic context of each occurrence of the seed sequence in the sequences of the target molecules. While the seed portion of the consensus target sequence has complete identity to a corresponding portion in each of the targeted binding sites, the consensus 3' flanking sequence need not be completely identical, but can be identical, to the sequencers flanking the 3' end of the seed of one or more of the target sequences. Likewise, the "consensus 3' flanking sequence" of the complement of the seed is readily derived by visual inspection, or through the use of bioinformatic tools or calculations, from the examination of the genetic context of each occurrence of the complement of the seed. While the complement of the seed portion of the consensus target sequence has complete identity to a corresponding portion in each of the targeted binding sites, the consensus 3' flanking sequence need not be completely identical, but can be identical, to the sequence/s flanking the 3' end of the complement of the seed.

Preferably, the consensus target sequence does not include any sequence that is predicted to have a propensity to undesirably modulate the expression or activity of one or more cellular component.

Consensus target sequences may be determined by eye or by algorithm. For example, a computer algorithm can be used to score all possible permutations of paired nucleotides in the positions in which the sequences are different. This is particularly useful when the target sequences have some identity beyond the seed, but for which an alignment by eye proves difficult. This method can be used to determine the consensus target sequence/s, or alternatively, directly design the strands of the candidate multitargeting interfering RNA.

One alternative approach that is particularly useful when a large number of target sequences need to be considered (e.g. when large numbers of nucleotide sequences for viral isolates are screened) is to generate all possible permutations of the extension from the seed to a required length, and/or the complete complement of the seed to a required length, thereby generating the putative Y'S' and/or XS of Formula (I) and hybridizing each putative XS and Y'S' against the target sequences of interest in silico to determine those which demonstrate the most favorable properties in terms of hybridization to the target.

Sequences demonstrating strong binding (typically having mean free energies of <−20 kcal/mol) are of particular interest for the multitargeting interfering RNA. Regardless of the flow path of design, the candidate XS and Y'S' are then prioritized for testing not only on this basis but also taking into account other features that may be important for the functionality of the multitargeting interfering RNA (by, for example, use of appropriate penalty terms). This may involve discarding those putative XS and Y'S' sequences which are composed of only a single base, are composed only of A and U, are predicted to be involved in substantial intramolecular base pairing, have a consecutive string of 5 or more bases which are G, are predicted to occur with unacceptable frequency in the antiparallel orientation in the non-target transcriptome of interest; are predicted to have a propensity to activate a cellular sensor of foreign nucleic acid, or any combination thereof.

In some cases, the addition of one or two nucleotides to the 5' end of the putative XS or Y'S' that are not complementary to their respective target sequences is considered. This is particularly relevant when an otherwise useful XS or Y'S' is G/C rich at the 5' end and this is predicted to disfavor loading relative to the other strand. The addition of one or two A/U nucleotides to the 5' extremity of the G/C rich XS or Y'S' will most likely promote balanced loading, which is required for optimal activity of the multitargeting RNA. Because multitargeting interfering RNAs in most cases tolerate mismatches at positions 1 and 2, the addition of this additional region, which need not be complementary to the corresponding target sequences, further increases the flexibility of design. Finally, one skilled in the art will appreciate that modifications that disfavor strand loading could be used on the 5' end of the strand present at the thermodynamically weaker end of the duplex to further enhance the loading of the opposite strand. Such modifications also include manipulation of the length and composition of the overhangs. Also, the substitution of U for C in the corresponding strand will at least partially rectify strand loading when there is a G near the 5' terminus of the XS or Y'S' by virtue of the wobble base pairing present between U and G, which is weaker than the pairing between C and G. Substitutions with chemically modified bases such as 2'F, 2'-O-methyl and LNA modified ribonucleotides increase the energy of hybridization of nucleotides with matching bases. Therefore, the alternative strategy of strengthening the hybridization of the duplex at the thermodynamically weaker end with chemically modified bases is also envisaged in this invention.

DNA sequences with stretches of contiguous guanosines are known to produce additional effects not related to targeting of mRNA. Although the situation in the case of RNA is less clear, most manufacturers recommend not selecting dsRNA duplexes containing long runs of G for their experiments. It was found in this invention that greater than 4 consecutive G greatly reduced the activity of the corresponding CODEMIR (data not shown). Therefore, many seeds could be eliminated if a requirement for 5 or more C is applied. One skilled in the art will recognize that the presence of 5 or more Cs in a seed will correspond to 5 or more Gs in the completely complementary RNA molecule of the invention.

In another embodiment, the method further comprises the step of discarding any consensus target sequence that: is composed of only a single base, is composed only of A and U, has a consecutive string of 5 or more bases which are C, is predicted to occur with unacceptable frequency in the non-target transcriptome of interest, is predicted to have a propensity to undesirably modulate the expression or activity of one or more cellular component, or any combination thereof.

Scanning the consensus target sequences against a transcriptome of interest for prediction of off-target effects, and eliminating any sequence predicted to have unacceptable off-target effects on a transcriptome of interest are also useful ways of reducing the number of consensus target sequences, and any of the foregoing may be added as a step in the process. In practice, it is prudent to routinely screen specific designed multitargeting interfering RNAs, e.g. CODEMIRs, VIROMIRs and the like, for cytotoxicity, due to unforeseen, but problematic, off-target effects.

Any undesirable properties for a therapeutic RNA, as would be understood by those of skill in the art, can be used as a basis on which to discard candidate seed sequences, consensus binding sites or proposed multitargeting interfering RNA.

Like candidate seeds and seeds, consensus target sequences are intermediates in the design of a multitargeting interfering RNA of the invention. In particular, the consensus target sequences are used to generate the sequences for the first and the second strand of a multitargeting interfering RNA of the invention. The first strand sequence is designed to comprise the first consensus target sequence and a complement of the consensus 3' flanking sequence of the second consensus target sequence, which is adjacent to and connected with the 5'-end of the first consensus target sequence. In a particular embodiment, the first strand is designed by extending the first consensus target sequence in the 5' direction with a complete complement of consensus 3' flanking sequence of the second consensus target sequence. The second strand sequence is designed to comprise the second consensus target sequence and a complement of the consensus 3' flanking sequence of the first consensus target sequence, which is adjacent to and connected with the 5'-end of the second consensus target sequence. In a particular embodiment, the second strand is designed by extending the second consensus target sequence in the 5' direction with a complete complement of consensus 3' flanking sequence of the first consensus target sequence.

In most cases, the overhangs, if required, are considered as part of the hybridization process. Hybridization is typically examined from a thermodynamic perspective using RNAhybrid software (Rehmsmeier et al., 2004, RNA, 10: 1507-17) or similar algorithm.

In particular embodiments, X and Y' in Formula (I) are completely complementary to their respective target sites. In the case in which the X and Y', by virtue of being simply complementary to their respective target sites result in very different G/C richness at the two ends, then the loading bias needs to be reduced by either producing mismatches in either X' or Y, depending on the thermodynamic balance. Alternatively, several chemical modifications (eg LNA, 2'O-methyl and 2° F. can be introduced into the "weak" end of the duplex to improve loading balance. Also, as shown in the Examples, varying the length of the overhang may be used to control the loading balance of the two strands of the duplex.

It will be readily appreciated by one skilled in the art that in the case of a double stranded multitargeting interfering RNA of the invention, ensuring similar strand loading of both strands is beneficial not only with respect to the potency of the molecule but is also required to obtain multitargeting activity. In a preferred embodiment, the multitargeting interfering RNA is designed such that there is no loading bias, so that both strands can load equally.

Various steps can optionally be added, individually or in combination, to further the rational process of designing the RNAs—such as to reduce the number of sequences unlikely to work for the intended purpose, to increase the effectiveness of the RNAs, to reduce off target effects and the like. Many of these steps can be automated, or require only a limited amount of input from an operator, though the use of bioinformatic computer systems, which as the skilled artisan will appreciate, will facilitate the methods.

Similar to the situation with antisense, for which it is now recognized that there are specific sequences that have a high propensity to activate cellular sensors of foreign DNA, other receptors may detect particular RNA sequences and produce stress responses (for example, see Sioud, M. (2005), *J Mol Biol* 348, 1079-1090. Specific "motifs" associated with increased inflammatory responses (Hornung, V. et al. (2005) *Nat Med* 11, 263-270; Judge, A. D. et al. (2005) *Nat Med* 11, 263-270) could be easily excluded.

In particular embodiments, the following sequences in the context of Formula (I) are discarded:

Occurrences of greater than 4 contiguous Gs in XSY or Y'S'X'

Greatly different G/C frequency in the X and Y regions (by function of duplex, this means also X' and Y') because loading bias is unlikely to be able to be equalized.

XS or Y'S' composed of only a single base or composed only of A and U or predicted to occur with unacceptable frequency in a non-target transcriptome of interest.

Where either of the strands are predicted to be involved in strong intramolecular base pairing.

Where the duplex comprises elements predicted or known to have a propensity to activate a cellular sensor of foreign nucleic acid.

In certain embodiments, the designed multitargeting interfering RNA molecule can be modified, for example, i) to improve actual or predicted loading of the strands of the multitargeting interfering RNA molecule into the RNA induced silencing complex (RISC); ii) to increase or decrease the modulation of the expression of at least one target RNA molecule; iii) to decrease stress or inflammatory response when the multitargeting interfering RNA molecule is administered into a subject; iv) to alter half-life in an expression system; or v) any combination of i) to iv).

The skilled artisan will understand how to modify the RNA molecules either in the laboratory, or preferably in silico. In preferred embodiments the modifying step comprises one or more of altering, deleting, or introducing one or more nucleotide bases to create at least one mismatched base pair, wobble base pair, or terminal overhang, or to increase RISC mediated processing. Techniques for doing so are known in the art. Preferably the modifications are at least initially performed in silico, and the effects of such modifications can be readily tested against experimental parameters to determine which offer improved properties of the interfering RNA products.

Also provided herein are methods that further comprise the step of actually making and testing at least one designed interfering RNA in a suitable cellular expression system. This will be necessary so as to identify those interfering RNA that have the required or sufficient activity against the target RNA molecules or that produce the required phenotype in the model system (eg death of cancer cell, inhibition of angiogenesis, suppression of lesion formation, accelerated wound healing etc).

In a presently preferred embodiment, the methods, through to the step of actually making an RNA, are conducted entirely in silico, or by visual inspection and determination. In one embodiment the method further comprises the step of choosing a new value for the seed length, n, and repeating each of the remaining steps. It is clear that the method can be iterative and the benefits of computers for such purposes are well known.

As will be appreciated, large numbers of seeds and thereby potential multitargeting interfering RNAs can be generated using the above methodology. While the rules above can be used to filter potential candidates based on undesirable properties, one skilled in the art will appreciate that with access to high throughput screening methodologies as well as recent improvements in quality, cost and access to RNA synthesis that testing of large numbers of candidates can be easily performed to further assist in the development of active multitargeting interfering RNAs. While the testing of a number of multitargeting interfering RNAs may be needed to identify those molecules with the greatest efficacy for a desired application, those skilled in the art of molecular biology will appreciate that this work does not amount to undue experimentation. Thus, it is occasionally preferable to screen significant numbers of candidates as opposed to prioritizing a few candidates solely on the basis of algorithmic design. A combination of careful in silico design along with biological testing of candidates can be used to identify candidates with superior activity in an efficient manner.

Screens that can be considered for the high throughput assessment of candidates include reporter assays, multiplexed ELISAs, viral replicon systems, dot-blot assays, RT-PCR etc.

Candidate multitargeting interfering RNA are routinely synthesized as double-stranded RNA molecules with 19 bp of complementarity and 3' two nucleotide overhangs. The overhang can be any nucleotides or analogs thereof, such as, for example, dTdT or UU. However, other types and lengths of overhangs could also be considered, as could "blunt-ended" duplexes. In a preferred embodiment, the overhangs are incorporated a priori into the design by having Y and X' being longer than the corresponding X and Y' by the length of the required overhangs.

When produced by an expression system such as a vector or plasmid, it is possible to assemble multiple multitargeting interfering RNAs into a single therapeutic product. Skilled artisans will realize that multiple multitargeting interfering RNAs can be co-expressed by several strategies, including but not limited to, expression of individual multitargeting interfering RNAs from multiple expression vectors (plasmid or viral), expression from multiple expression cassettes contained within a single vector, with each expression cassette containing a promoter, a single multitargeting interfering RNA and terminator. Multiple multitargeting interfering RNAs can also be generated through a single polycistronic transcript, which contains a series of multitargeting interfering RNAs.

The multitargeting interfering RNAs can be expressed sequentially (sense/intervening loop/antisense) or expressed with the sense sequence of each multitargeting interfering RNA sequentially linked 5' to 3', joined directly or with intervening loop/spacer sequence, followed by the antisense sequence of each multitargeting interfering RNAs sequentially linked 5' to 3'.

In the first instance, multitargeting interfering RNA are typically tested in cell culture using an appropriate cell line representative of the targeted tissue. The specific conditions used are outlined in the specific examples. Multitargeting interfering RNA that lead to reduction in target RNA expression can then be studied further. Specifically, semi-quantitative RT-PCR for the target RNA may be performed to establish whether modulation of expression of a target RNA is likely to be mediated by degradation. In general, cells are transfected with the multitargeting interfering RNA at a concentration of 5-40 nM in the culture medium and after 48 hours, are washed, trypsinized and harvested for total RNA using a RNeasy kit (Qiagen). RT-PCR is then performed using primer sets specific for the target RNAs.

Proteomic and microarray experiments may be used to assess off-target effects. Likewise, to select active multitargeting interfering RNA with little propensity for activation of innate immune response, analysis of markers of IFN-response (eg STAT1, IFNb, IL-8, phosphoEIF etc) can be performed on treated cells.

Preferably, the candidate multitargeting interfering RNA are tested for non-specific toxic effects by, for example, direct assays of cell toxicity. Alternatively, in some cases such as cancer, cytotoxicity is the desired outcome and may reflect the successful repression of key oncogenic signaling pathways. Multitargeting interfering RNA are additionally assessed for their ability to repress the production of specific target proteins. Multitargeting interfering RNA demonstrating efficacy in this respect are then assessed for additional evidence of off-target effects, including arrest of non-target protein production and activation of Protein Kinase R (PKR) mediated responses.

The RNA molecule may be expressed from transcription units inserted into vectors. The vector may be a recombinant DNA or RNA vector, and includes DNA plasmids or viral vectors. The multitargeting interfering RNA molecule expressing viral vectors can be constructed based on, but not limited to, adeno-associated virus, retrovirus, adenovirus, lentivirus or alphavirus.

Preferably the vector is an expression vector suitable for expression in a mammalian cell.

Methods which are well known to those skilled in the art can be used to construct expression vectors containing a sequence which encodes the multitargeting interfering RNA molecule. These methods include in vitro recombinant DNA techniques, synthetic techniques and in vivo recombination or genetic recombination. Such techniques are described in Sambrook et al (1989) Molecular Cloning, A laboratory manual, Cold Spring Harbor Press, Plainview N.Y. and Asubel F M et al (1989) *Current Protocols in Molecular Biology*, John Wiley & Sons, New York N.Y. Suitable routes of administration of the pharmaceutical composition of the present invention may, for example, include oral, rectal, transmucosal, or intestinal administration; parenteral delivery, including intramuscular, intravenous and subcutaneous injections.

Alternatively, the pharmaceutical composition may be administered in a local rather than systemic manner, for example, via injection of the pharmaceutical composition directly into a target organ or tissue, such as intramedullary, intrathecal, direct intraventricular, intraperitoneal, or intraocular injections, often in a depot or sustained release formulation. Intravesicular instillation and intranasal/inhalation delivery are other possible means of local administration as is direct application to the skin or affected area. Ex vivo applications are also envisaged.

Furthermore, the pharmaceutical composition of the present invention may be delivered in a targeted delivery system, for example, in a liposome coated with target cell-specific antibody. The liposomes will be targeted to and taken up selectively by the target cell. Other delivery strategies include, but are not limited to, dendrimers, polymers, nanoparticles and ligand conjugates of the RNA.

The multitargeting interfering RNA molecule of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers.

In another aspect, the invention provides biological systems containing one or more multitargeting interfering RNA molecule of this invention. The biological system can be, for example, a virus, a microbe, a plant, an animal, or a cell. The invention also provides a vector comprising a nucleotide sequence that encodes the multitargeting interfering RNA molecule of the invention. In particular embodiment, the vector is viral, for example, derived from a virus selected from the group consisting of an adeno-associated virus, a retrovirus, an adenovirus, a lentivirus, and an alphavirus. The multitargeting interfering RNA can be a short hairpin RNA molecule, which can be expressed from a vector of the invention. The invention further provides a pharmaceutical composition comprising a multitargeting interfering RNA molecule of the invention and an acceptable carrier. In particular embodiments, the pharmaceutical composition comprises a vector for a multitargeting interfering RNA molecule of the invention.

In another general aspect, the present invention provides a method of inducing RNA interference in a biological system, which comprises the step of introducing a multitargeting interfering RNA molecule of the invention into the biological system.

The invention further comprises a method of treating a subject, comprising the step of administering to said subject a therapeutically effective amount of a pharmaceutical composition comprising a multitargeting interfering RNA molecule of the invention. The invention also provides a method of inhibiting the onset of a disease or condition in a subject, comprising administering to said subject a prophylactically effective amount of a pharmaceutical composition comprising a multitargeting interfering RNA molecule of the invention. Methods are known in the art for determining therapeutically and prophylactically effective doses for the instant pharmaceutical composition.

The compositions and methods exemplified herein are of use in the treatment of complex multigenic diseases in which single gene-specific therapeutics may be at a disadvantage because of the multiple redundancies in pathophysiologic signaling pathways. A conscious and calculated approach is provided in which key signaling proteins/pathways can be simultaneously targeted with a single agent to generate greatly increased therapeutic potential.

In some cases, the targets of interest may be at least partially controlled by a common "master regulator". This is usually a transcription factor. For example, down-regulation of IL-8 and MCP-1 might be achievable through targeting the nuclear factor NFkappaB. However, as an example, this pathway is also involved in the survival of Retinal Pigmented Epithelial cells (RPE) in times of stress and the down regulation of such a cell-survival factor would likely lead to increased death of RPE in diseased eyes. Therefore, the novel approach disclosed herein has the advantage of being amenable to the modulation of specific targets of interest without having to identify suitable target "upstream" pleiotropic controllers.

Application also exists in the treatment of diseases characterized by cellular heterogeneity. For example, in solid tumours, the presence of mutated genes and activated pathways may vary widely within the same tumour, between tumours in the same patient as well as between tumours of a similar histology in different patients. In such instances, the development of an RNA molecule active against several key pathways may derive synergistic activity against cells reliant on several of these targeted pathways. However, activity against a greater proportion of the tumour cells will also be likely because of the "multi-targeted" nature of the RNA molecule of the invention. Furthermore, targeting of several key pathways will "cover" more of the patient population. Hence, improved clinical outcomes are likely with treatment with the RNA molecules exemplified or taught herein.

In cases in which RISC is involved in the mechanism of action, the targeting of multiple disease-related transcripts with a single multitargeting interfering RNA molecule of the invention (eg a CODEMIR or VIROMIR) preferably allows full use of available RISC as opposed to the administration of multiple siRNA molecules, which could, in some cases, saturate the available intracellular machinery.

Targeting multiple sites within the same RNA target sequence can also be accomplished with the compositions and methods provided herein. Many human diseases, including cancer and viral infections, are characterized by RNA targets exhibiting high mutation rates. This increases the likelihood of resistance to nucleic acid therapeutics arising in these diseases, due to mutation of the target RNA. Targeting multiple sites within the target RNA decreases the likelihood of such resistance arising, since at least two simultaneous mutations would be required for resistance. In this instance, therefore, the multi-targeting approach of multitargeting interfering RNAs (eg CODEMIRs or VIROMIRs) is directed to the generation of multiple hits against a single target RNA to prevent escape mutants. Targeting of multiple sites within the same transcript (eg. as in the case of RNA viruses) may also produce synergistic effects on the inhibition of viral growth. Further, employing a mechanism or mechanisms requiring only partial complementarity with the target RNA can have an advantage in decreasing the possibility of developing resistance through point mutation.

The desired targets for any disease entity may be identified based on an approach or a mixture of approaches including, but not limited to, validated drug targets from literature and proprietary target discovery processes. The target genes are then prioritized based on evidence supporting a key role for their products in the disease process of interest.

In some cases, specific attention may need to be paid to the accuracy and/or relevance of the sequence to the disease of interest. For example, in targeting cancer, it is advisable to avoid mutational "hot-spots". Also, in some embodiments, selective targeting of a specific splice variant or isoform may be desired and thus in such embodiments, the target sequence used in multitargeting interfering RNA design is preferably restricted to that isoform or variant present only in diseased tissue.

The sequences of the target RNA or RNAs are preferably downloaded from public or proprietary databases or generated from sequencing experiments.

EXAMPLE 1

CODEMIRs to VEGF-A and ICAM-1

Approaches for the design of multi-targeting of ICAM-1 and VEGF-A with CODEMIRs were considered.

The entire mRNA sequence for each of VEGF-A and ICAM-1 was used. These sequences were searched to find sequences that are present in the coding strand for one target and the complement of the coding strand for another target. Here, the sequence 5'-AGTGACTGTCAC-3' (SEQ ID NO: 1) was identified both in the ICAM-1 coding sequence and in the complement of the VEGF-A coding sequence. This sequence was used to design a CODEMIR active against multiple targets, using each strand of the CODEMIR to target at least one of the target RNAs. The sequence identified above and its complement were used as a centrally-located part of a CODEMIR duplex. Each strand of this central duplex was extended in the 5' direction to provide full complementarity to the corresponding target, whereas each strand was extended in the 3' direction so as to be complementary to its opposing strand in the CODEMIR duplex strand.

The skilled artisan will appreciate that rationally designing CODEMIRs requires designing portions of both strands (as a duplex) together and gradually lengthening the duplex, and refining to complete the design. The rational design process can continue after the duplex is largely complete—as the refinements may be made to modify the ends, or to create mismatches or wobble pairings to improve loading or other aspects of functionality.

The length of this central region (12 nt) leads to two possible 21-base duplexes with 3' double overhangs depending on how the remaining required sequence is divided into the two sequences surrounding the seed. Each of those CODEMIRs is shown in Table 1-1 (CODEMIRs-16 and -17).

It will be appreciated by one skilled in the art that these CODEMIRs comprise a sequence that is the complement of the seed. In this example, the complementary sequence in the CODEMIRs is GUGACAGUCACU. (SEQ ID NO: 2)

CODEMIRs-16 and -17 were tested for activity against both VEGF-A and ICAM-1 targets in RPE cells. RPE cells in culture were used to screen the anti-angiogenic CODEMIRs designed, as described above. The human cell line, ARPE-19, was used. ARPE-19 cells were grown in Dulbecco's Modified Eagle's Medium supplemented with 10% fetal bovine serum and 10 mM glutamine. For ELISA detection of secreted proteins of interest, or in situ cell surface antigen immunostaining, ARPE cells were seeded at $4 \times 10^3$ cells per well in a 96 well tissue culture plate. For FACS analysis, ARPE-19 cells were seeded at $2.5 \times 10^4$ cells per well in a 24 well tissue culture plate. Cells were transfected 24 hours after seeding using lipofectamine (InVitrogen) at a ratio of 1 microL lipofectamine per 20 μmol of CODEMIR RNA duplex or control siRNA. In most studies, medium was replaced 24 hours after transfection at which time deferoxamine (130 μM) or IL-1β (1 ng/mL) was added for the VEGF-A and ICAM-1 experiments, respectively. Experiments were performed in triplicate and repeated at least twice.

The ARPE-19 cells were assayed to confirm production of both VEGF-A and ICAM-1. VEGF-A was assayed in the supernatant using a commercially available ELISA assay (R&D Systems) according to the manufacturer's instructions. Cell surface ICAM-1 was assayed either by immunostaining followed by fluorescence activated cell sorting (FACS), by in situ immunostaining of cell-surface ICAM-1 in 96 well plates using colorimetric detection, or alternatively by ELISA of cell lysates using a commercial sICAM ELISA kit (R&D systems).

The results are shown in FIG. 1. Both CODEMIRs were active modulators of the multiple targets. CODEMIR-16 was more active in modulating VEGF-A and CODEMIR-17 was more active against ICAM-1, apparently as a result of the design symmetry. This is likely due to altered strand-loading bias.

The loading bias can be adjusted, for example, by introducing wobble G:U basepairs into the extremities of the duplex, or by expanding the CODEMIR to a 22-base duplex with symmetrical extremities. Variations of each of these types were explored. CODEMIR-26 is a 22-base duplex that has 4 identical binding nucleotide pairs at each of the two termini of the duplex. As shown in FIG. 1, CODEMIR-26 exhibited greatly increased ICAM-1 targeting compared to that of CODEMIR-16. Thus, the adjustments to the sequence were able to correct the loading bias observed with CODEMIR-16.

CODEMIRs-27 and -28 (see Table 1-1) were designed to test whether disrupting strong G:C pairs at an end of the duplex region would also successfully overcome the loading bias observed with CODEMIR16. As can be seen from the results in FIG. 1, the substitution of a C with a U in the 3' terminal region of the guide strands targeting VEGF-A was successful in changing the bias (e.g. CODEMIR-27). CODEMIR-28 had similar activity to CODEMIR-27 where changes were made at the other end of the CODEMIR.

It was also envisaged herein that both strand loading bias and target activity can be controlled by introducing mismatches to disrupt the end of the duplex that is inefficiently loaded and simultaneously increase hybridization to the target. For example, in CODEMIR-36, a variant of CODEMIR-16, both strands were designed to be entirely complementary to the respective target sequences; the resulting incompletely complementary duplex features several mismatches at the 5' extremity of the ICAM-1 guide sequence. The results for CODEMIR-36 (see Table 1-1) are shown in FIG. 1.

The multitargeting interfering RNA (CODEMIRs) herein disclosed would be expected to be effective in multiple angiogenic diseases of the eye. This is because secreted VEGF-A plays a major role in all of these diseases (Witmer et al (2003) *Prog Retin Eye Res,* 22, 1-29), although ICAM-1 overexpression may be an early initiating event, particularly for diabetic retinopathy and macular edema (Funatsu et al., (2005) Opthalmology, 112, 806-16.; Joussen et al. (2002) *Am J Pathol,* 160, 501-9; Lu et al. (1999) *Invest Opthalmol Vis Sci,* 40, 1808-12. We have shown that several CODEMIRs are able to suppress both VEGF-A and ICAM-1 production by human retinal epithelium cells (ARPE-19 cell line). These cells are a major contributor to the production of these proteins in these ocular angiogenic diseases (Matsuoka et al., (2004) *Br J Opthalmol,* 88, 809-15, Yeh et al. (2004), *Invest Opthalmol Vis Sci,* 45, 2368-73). RPE cells are also the primary site of uptake of foreign nucleic acids in the eye and, for these two reasons, are the appropriate cell model for evaluation of anti-angiogenic CODEMIRs in opthalmology. The in vivo activities of two oligonucleotide drugs correlated with their activity against RPE cells in culture (Garrett et al. (2001) *J Gene Med,* 3, 373-83; Rakoczy et al. (1996), *Antisense Nucleic Acid Drug Dev,* 6, 207-13) demonstrating the value of this cell culture model. An advantage of this cell line is that it forms polarized monolayers that mimic the RPE layer of the eye (Dunn et al., (1996), *Exp Eye Res,* 62, 155-69).

TABLE 1-1

Design of CODEMIRs for the targeting of VEGF-A and ICAM-1

Top strand 5' to 3'
Bottom strand 3' to 5'     VEGF binding*              ICAM binding*

CODEMIR16

```
ICAM Guide                 5' G                  U 3'  5' C       AAUC            A 3'
CGAGUGACAGUCACUAGCUCC         AUCG GUGACAGUCACUAGCU       GGGG    AGUGACUGUCACUCG
(SEQ ID NO: 3)             (SEQ ID NO: 5)               (SEQ ID NO: 6)
UAGCUCACUGUCAGUGAUCGA         UAGC CACUGUCAGUGAUCGA       CCUC    UCACUGACAGUGAGC
(SEQ ID NO: 4)             3'        U 5'                3'       GA                   5'
VEGF Guide                 (SEQ ID NO: 4)               (SEQ ID NO: 3)
```

CODEMIR17

```
ICAM Guide                 5' U                  U 3'  5' G       AAUC            G 3'
UCGAGUGACAGUCACUAGCUC         GAUCG GUGACAGUCACUAGC       GGG     AGUGACUGUCACUCGA
(SEQ ID NO: 7)             (SEQ ID NO: 9)               (SEQ ID NO: 10)
CUAGCUCACUGUCAGUGAUCG         CUAGC CACUGUCAGUGAUCG       CUC     UCACUGACAGUGAGCU
(SEQ ID NO: 8)             3'        U              5'  3'        GA                  5'
VEGF Guide                 (SEQ ID NO: 8)               (SEQ ID NO: 7)
```

CODEMIR26

```
ICAM Guide                 5'U                   U 3'  5' C       AAUC            G 3'
UCGAGUGACAGUCACUAGCUCC        GAUCG GUGACAGUCACUAGCU      GGGG    AGUGACUGUCACUCGA
(SEQ ID NO: 11)            (SEQ ID NO: 67)              (SEQ ID NO: 13)
CUAGCUCACUGUCAGUGAUCGA        CUAGC CACUGUCAGUGAUCGA      CCUC    UCACUGACAGUGAGCU
(SEQ ID NO: 12)            3'        U              5'  3'        GA                  5'
VEGF Guide                 (SEQ ID NO: 12)              (SEQ ID NO: 11)
```

TABLE 1-1-continued

Design of CODEMIRs for the targeting of VEGF-A and ICAM-1

Top strand 5' to 3'
Bottom strand 3' to 5'      VEGF binding*                    ICAM binding*

CODEMIR27

```
ICAM Guide                5'  G                      U 3'    5' C      AAUC               A 3'
CGAGUGACAGUCACUAGCUCC            AUCG GUGACAGUCACUAGCU             GGGG    AGUGACUGUCACUCG
(SEQ ID NO: 3)            (SEQ ID NO: 5)                     (SEQ ID NO: 6)
UAGUUCACUGUCAGUGAUCGA            UAGU CACUGUCAGUGAUCGA             CCUC    UCACUGACAGUGAGC
SEQ ID NO: 14)            3'      U                  5'    3'      GA                   5'
VEGF Guide                (SEQ ID NO: 14)                    (SEQ ID NO: 3)
```

CODEMIR28

```
ICAM Guide                5' U                       U 3'    5' G      AAUC               G 3'
UCGAGUGACAGUCACUAGUUC          GAUCG GUGACAGUCACUAGC              GGG    AGUGACUGUCACUCGA
(SEQ ID NO: 15)           (SEQ ID NO: 9)                     (SEQ ID NO: 10)
CUAGCUCACUGUCAGUGAUCG          CUAGC CACUGUCAGUGAUCG              CUU    UCACUGACAGUGAGCU
(SEQ ID NO: 8)            3'      U                  5'    3'      GA                   5'
VEGF Guide                (SEQ ID NO: 8)                     (SEQ ID NO: 15)
```

CODEMIR36

```
ICAM Guide                5' U                       U 3'    5' G                         A 3'
   CGA       A                GAUCGGUGACAGUCACUAGCU               GGAAUCAGUGACUGUCACUCG
GUGACAGUCACUG UUCC        (SEQ ID NO: 67)                    (SEQ ID NO: 18)
(SEQ ID NO: 16)               CUAGCCACUGUCAGUGAUCGA              CCUUAGUCACUGACAGUGAGC
CUAGCCACUGUCAGUGAUCGA     3'                         5'    3'                             5'
(SEQ ID NO: 17)           (SEQ ID NO: 17)                    (SEQ ID NO:16)
VEGF Guide
```

* Upper strand=mRNA target, lower strand=CODEMIR guide strand. The bold sequence identifies the sequence present in ICAM-1 and as its complement in VEGF-A around which the CODEMIR duplexes were designed.

EXAMPLE 2

CODEMIRs to Gluc6P and Inppl1

CODEMIRs may also be suitable for the treatment of complex metabolic diseases such as type 2 diabetes. Two potential gene targets for the treatment of this disease are glucose-6-phosphatase and Inppl1. Full transcript sequences were examined. Candidate CODEMIRs from the best contiguous region of identity are shown for each case in Table 2-1.

Figure 2:
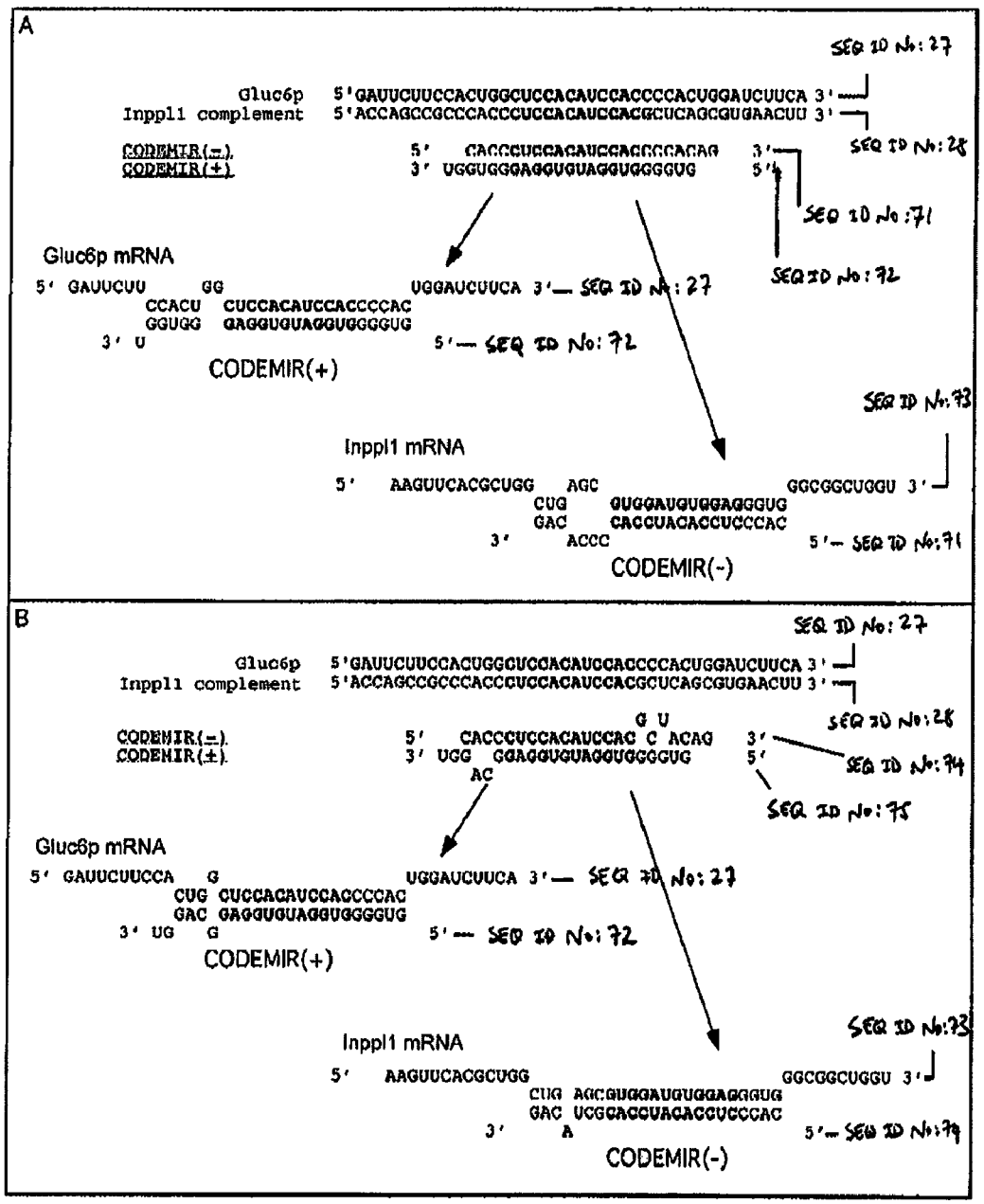
FIG. 2 Panel A: Further exemplification of multitargeting using both strands of a CODEMIR duplex in which the CODEMIR duplex strands may be completely complementary to each other. Any overhangs present will be without complementary base pairing. Panel B: An example of a CODEMIR showing incomplete complementarity between the two active strands of the CODEMIR. Such incomplete complementarity, can derive, for example, by virtue of each strand being completely complementary or almost completely complementary to its respective target.

Regions of complementarity between the two targets were found and the two identified seeds (Table 2-1: CUGC-CUCGCCCAG (SEQ ID NO: 19) and CUCCACAUCCAC) (SEQ ID NO: 20) were used as the central motifs for two possible CODEMIR duplexes. The latter seed and its complement were extended at their 5' ends to generate duplexes in which each strand has 5' complementarity to one of the target sequences (FIG. 2A). This is important because both strands of the CODEMIR duplex are effectors and an increased region of identity of each strand with its target needs to be extended to the 5' terminus, whereas the less critical 3' end requires less complementarity (FIG. 2A). Some modification of the CODEMIRs can be performed to tune the hybridization of the CODEMIR duplex, thereby affecting the loading bias. Introduction of mismatches is one way of achieving this (for example see: Ohnishi et al. (2005) *Biochem Biophys Res Commun.* 329:516-21) and these mismatches can be chosen also for their ability to increase binding of the 3' region of the effector strands to their respective target transcripts (FIG. 2B). In this situation, the CODEMIR duplex is then no longer composed of two strands with complete complementarity, similarly to CODEMIR-36.

It will be appreciated by one skilled in the art that multi-targeting interfering RNA molecules (CODEMIRs) will comprise the sequence corresponding to the complement of the seed. In this example, these complementary sequences are CUGGGCGAGGCAG (SEQ ID NO: 21) and GUG-GAUGUGGAG. (SEQ ID NO: 22)

TABLE 2-1

Target sequences aligned with CODEMIRs for
targeting Gluc6p and Inppl1.

Sequences

```
Gluc6p              5' GUGUCAUCCCCUACUGCCUCGCCCAGGUCCUGGGCCAGC 3'      (SEQ ID NO: 23)
Inppl1 (complement) 5' CAGGCACUCAUGCCUGCCUCGCCCAGCCCGCUGGCCCGC 3'      (SEQ ID NO: 24)
```

Candidate CODEMIR duplex 1 (e.g. central duplex 1)

```
Inppl1 targeting strand   5' AUGCCUGCCUCGCCCAGGUCC 3'        (SEQ ID NO: 25)
Gluc6p targeting strand   3' UACGGACGGAGCGGGUCCAGG 5'        (SEQ ID NO: 26)
```

TABLE 2-1-continued

Target sequences aligned with CODEMIRs for targeting Gluc6p and Inpp11.

| | Sequences | |
|---|---|---|
| Gluc6p | 5' GAUUCUUCCACUGGCUCCACAUCCACCCCACUGGAUCUUCA 3' | (SEQ ID NO: 27) |
| Inpp11 (complement) | 5' ACCAGCCGCCCACCCUCCACAUCCACGCUCAGCGUGAACUU 3' | (SEQ ID NO: 28) |
| Candidate CODEMIR duplex 2 (e.g. central duplex 2) | | |
| Inpp11 targeting strand | 5' CACCCUCCACAUCCACCCCAC 3' | (SEQ ID NO: 29) |
| Gluc6p targeting strand | 3' GUGGGAGGUGUAGGUGGGGUG 5' | (SEQ ID NO: 30) |

EXAMPLE 3

VIROMIRs Targeting Multiple Sites within the HIV Genome

The invention can be used to target proteins of interest that are likely to be mutated in chronic forms of disease. Mutations may be particularly prevalent in cancer and viral disease in which drug-resistant forms often evolve. In this example, VIROMIRs were designed to target multiple sites in the Human Immunodeficiency Virus (HIV). The requirement for simultaneous mutation at several sites, in order to overcome the effects of such a VIROMIR, is likely to provide a high genetic hurdle to the emergence of resistant viral clones or quasispecies. The genome of the HXB2 strain of HIV I serotype B (GenBank Accession K03455) was used as the principal sequence of interest and was examined with bioinformatics methods detailed elsewhere in this application to find seeds occurring at more than one location. All HIV I clade B isolates in the LANL database as of 1 Aug. 2005 which contain full sequences for any of the GAG, ENV, POL, TAT, VIF, VPR, VPU and NEF genes were used in these analyses.

A 17-base seed and its complete complement were found in the HIV reference strain genome as shown below:

(SEQ ID NO:31)
TCTAATTCCAATAATTCTTGTTCATTCTTTTCTTGCTGGTTTTGCGATTC

TTCAATTAAGGAGTGTATTAAGCTTGTGTAATT K03455r (SEQ ID NO:32)
CTTTGAGCCAATTCCCATACATTATTGTGCCCCGGCTGGTTTTGCGATTC

TAAAATGTAATAATAAGACGTTCAATGGAACAG K03455 wherein, K03455r is a partial sequence of the complement of the reference strain genome.

In the population of Clade B isolates described above, the seed (GCTGGTTTTGCGATTCT) (SEQ ID NO: 33) was found in 76% of isolates, whereas its complement (AGAATCGCAAAACCAGC) (SEQ ID NO: 34) was found in 4% of isolates respectively.

Ultimately, an effective RNA therapeutic of the invention should provide broad coverage of the affected population and it is obviously desirable to target sequences that are highly represented in this patient population. Therefore, the seed presented above might not cover a sufficient proportion of the population. Nevertheless, due to its unique size it was considered further in the exemplification of the invention.

However, if conservation needed to be improved for this seed, one skilled in the art would appreciate that using a sub-segment of this seed could result in improved conservation. For example, when two bases are removed, as in the following:

| 5' TGGTTTTGCGATTCT 3' | (forward) | (SEQ ID NO:35) |
|---|---|---|
| 5' AGAATCGCAAAACCA 3' | (reverse) | (SEQ ID NO:36) | the forward conservation remains at 76%, while the reverse conservation increases substantially to 35%.

In order to prioritize and test candidate VIROMIRs, it is important to have screening methods that are compatible with the intended target sequence. The pNL4.3 assay is widely used in the field of HIV research as a valuable, validated screen for drugs active in HIV and was used by us to test candidate VIROMIRs. However, there are some differences between the sequences of the HIV component of the pNL4.3 plasmid and that of the reference HIV strain (K03455) used in the design of the VIROMIR. Therefore, comparison of the sequence of the reference strain and the sequence of the pNL4.3 plasmid was carried out to confirm that the above-mentioned VIROMIR was targeting a sequence also present in the testing system. Other testing systems such as viral challenge assays, fusion reporters, viral pseudoparticles among others, each representing any multitude of therapeutically relevant or irrelevant sequences could equally be considered.

An example of a VIROMIR duplex (VM011) targeting these two seed sites is:

| 5' UGCUGGUUUUGCGAUUCUAAA 3' | (SEQ ID NO: 37) |
|---|---|
| 3' GAACGACCAAAACGCUAAGAU 5' | (SEQ ID NO: 38) |

Analyzing the ends of the duplex, it will be apparent to one skilled in the art that the two strands would be unlikely to load equally, given the greater G/C content at one end relative to the other, therefore it would likely benefit from further optimization as discussed elsewhere in this invention.

HIV generally causes chronic infection with in vivo viral reservoirs. Consequently, VIROMIRs targeting HIV are most likely to be therapeutically effective as cell-expressed short hairpin RNAs (shRNAs) rather than as synthetic RNA duplexes because of a need for continued therapeutic cover to prevent re-emergence from latent sites.

The sequences for VM011 were used in the design of an shRNA. Contiguous DNA sequences corresponding to: BamHI restriction site, G initiator, VIROMIR passenger, Xho loop sequence (ACTCGAGA), VIROMIR guide strand, polIII terminator and HindIII restriction site were assembled and prepared as dsDNA. They were then cloned into a pSIL vector under the control of a H1 promoter. The resulting double-stranded DNA insert designed to encode an shRNA VIROMIR approximating VM011 is shown below (loop sequence in parentheses and terminator italicized):

```
                                              (SEQ ID NO: 39)
5' GATCCGCTTGCTGGTTTTGCGATTCTA(ACTCGAGA)TAGAATCGCA

AAACCAGCAAGTTTTTGGAA
                                              (SEQ ID NO: 40)
       GCGAACGACCAAAACGCTAAGAT(TGAGCTCT)ATCTTAGCGT

TTTGGTCGTTCAAAAAACCTTTCGA-5'
```

One skilled in the art will appreciate that when transcribed, the encoded RNA folds into a hairpin structure, which is modified by the cellular Drosha and Dicer proteins to generate active VIROMIR RNA duplex(es). The skilled artisan will also recognize that a number of variations of the design of the shRNA construct could be considered. These include but are not limited to: length, sequence and orientation of the shRNA duplex components (guide strand, passenger strand, precursors), length and sequence of the loop, choice of promoter, initiator and terminator sequences as well as the cloning strategies used to assemble the final construct.

This shRNA construct was tested in HEK-293 cells by co-transfecting with the pNL4.3 plasmid. Specifically, HEK-293 cells were seeded at density of 2×10^5 cells in 1 ml Optimem medium/well in a 12-well plate. Cells were transfected 24 hr later with 200 µL DNA: Lipofectamine mix (200 ng pNL4.3 plasmid, 67 ng VIROMIR pSIL construct in 100 µL complexed with 2.7 µL Lipofectamine 2000 in Optimem). After changing the medium 24 hours later, the production of p24 was assayed by collection of the supernatant after a further 24 hours of incubation.

The production of p24 was expressed as a percentage of the production from cells transfected with the empty control plasmid. VM011 did not have any appreciable activity in this assay (data not shown), perhaps reflecting the lack of equivalent loading, as predicted from the analysis of the ends of the duplex. Nevertheless, one skilled in the art will appreciate that other design strategies (eg. alternative extension of the strands from the seed and its complement, or variation of the shRNA construct as described above) could be considered for the development of an active VIROMIR of this design, which when combined with appropriate screens such as the one used above, could be used to identify useful therapeutics.

EXAMPLE 4

Dual Targeting of HCV and TNFa

In some cases of infectious diseases, multitargeting interfering RNAs can be utilized to target both the genome of the infectious agent and one or more key host "drivers" of the disease. For example, TNF-alpha is considered a major disease-associated factor in Hepatitis C Virus infection and its sequelae. Investigation of the genome of HCV and the TNF-alpha mRNA was undertaken.

On searching for 9 base seeds and their complete complements in HCV and TNFa, the following seed of interest was one of several identified: 5' ACTCCCCTG 3' (SEQ ID NO: 41)

This seed was selected because it is present in the HCV genome with a conservation of 94% in 155 isolates of genotypes 1a and 1b. This seed is actually present in two sites in HCV. We then considered the nucleotides in the 3' direction from this seed to establish which site should be primarily considered in the design of the duplex. The extended sequences for the sites (+6 bases to the 3' end) were as follows:

```
ACTCCCCTGTGAGGA   (site #1)   (SEQ ID NO: 42)

ACTCCCCTGACGCCG   (site #2)   (SEQ ID NO: 43)
```

It was found that the rate of occurrence of the seed at the first site was much higher than at the second (92% vs 7%). Therefore the further design of the multitargeting interfering RNA was performed only considering the sequence of the 1st site.

In genetic context terms, the seed is in the 5'NTR of HCV and 3'UTR of TNFalpha. Shown below is the location of the seed in the HCV sequence and in the antiparallel sequence for TNFalpha:

```
                                                  (SEQ ID NO: 44)
5' TGATGGGGGCGACACTCCACCATGAATC ACTCCCCTG    HCV

TGAGGAACTACTGTCTTCACGCAGAAAGC 3'

(SEQ ID NO: 45)
3' ACTGAATAGTAGGGCGATTACAGACACA ACTCCCCTG    TNFar

GGGAGCAGAGGCTCAGCAATGAGTGACAG 5'
```

Because the seed is 9 mer, the required extension for the duplex of the required length (eg 19) is, for example, 5 bases in the 3' direction of the target and 5 bases in the 5' direction as the seed is usually in the middle of the double stranded duplex (excluding the overhangs). By putting it in the middle, the resulting two strands will have an equivalent portion of complete complementarity with their respective targets when the process outlined below is followed. This should ensure that binding of the resulting two strands should be comparable. With a seed of, for example, ten nucleotides, the extension by 5 on each side would create a duplex of 20, whereas extension of 4 plus 5 or 5 plus 4 would yield a duplex of 19 nucleotides. Other permutations are equally permissible depending on the lengths of the seed and the desired duplex.

In this example, a means of generating one of the strands of the duplex is as follows:

- Starting with the complement of the seed of the target in the normal orientation (i.e. HCV) gives the following sequence 5' CAGGGGAGU 3'. (SEQ ID NO: 46)
- Then extend this sequence further in its 5' direction by taking the complement of the next 5 bases of the HCV sequence at the 3' end of the seed—this gives 5' CCU-CACAGGGGAGU 3'. (SEQ ID NO: 47)
- This is followed by the addition of the complement of the next 5 bases of the second target which is in the antiparallel orientation (i.e. TNFa) to give the first strand sequence of 5'-CCUCACAGGGGAGUUGUGU-3' (SEQ ID NO: 48)
- The opposite strand (TNFa) is then the complement of the first guide strand: 5'-ACACAACUCCCCUGUGAGG-3' (SEQ ID NO: 49)

such that the duplex is:

```
5'-CCUCACAGGGGAGUUGUGU-3'    (SEQ ID NO: 48)

3'-GGAGUGUCCCCUCAACACA-5'    (SEQ ID NO: 49)
```

The two guide strands have predicted binding to the two targets of:

```
HCV    5' G     UCCACCAUGAAUC               A 3'
         ACAC             ACUCCCCUGUGAGG      (SEQ ID NO: 50)
         UGUG             UGAGGGGACACUCC
Guide#1 3'    U                          5'   (SEQ ID NO: 48)
mfe: -35.0 kcal/mol
TNFa   5' G      UGCUCCC              C 3'
          CCUC       CAGGGGAGUUGUGU           (SEQ ID NO: 51)
          GGAG       GUCCCCUCAACACA
Guide#2 3'     U                     5'       (SEQ ID NO: 49)
mfe: -35.0 kcal/mol
``` above in silico binding result a large bulge is predicted to be formed from the binding of the first guide strand to the HCV target RNA. The choice of overhangs could be guided by the desire to reduce the length of that bulge. Other alternatives are to add bases complementary to the target to provide an extension of the binding indicated in silico. So, as an example, the duplex generated above could be further extended using the information from the in silico hybridization to further define the bases required.

```
5'-CCUCACAGGGGAGUUGUGCCC-3'    (SEQ ID NO: 57)
3'-UCGGAGUGUCCCCUCAACACG-5'    (SEQ ID NO: 58)
```

Alternatively, the sequence could be empirically extended by adding UU:

```
5'-CCUCACAGGGGAGUUGUGCUU-3'    (SEQ ID NO: 59)
3'-UUGGAGUGUCCCCUCAACACG-5'    (SEQ ID NO: 60)
```

To improve equality of loading, the duplex could be extended with further complementarity to the HCV sequence, possibly:

```
5'-UCCUCACAGGGGAGUUGUGU-3'   (SEQ ID NO: 52)

3'-AGGAGUGUCCCCUCAACACA-5'   (SEQ ID NO: 53)
```

This has the effect of producing a more balanced representation of weak (A:U) and strong (G:C) base pairs at the ends of the duplex.

Alternatively, a duplex for which the TNFa-targeting strand is mutated but still capable of binding to the target and the corresponding strand is changed to match could be:

```
5'-CCUCACAGGGGAGUUGUGC-3'    (SEQ ID NO: 54)

3'-GGAGUGUCCCCUCAACACG-5'    (SEQ ID NO: 55)
```

In this situation, the first 5 base pairs of the duplex are equally balanced at the two ends, without appreciably compromising binding to the target as shown below (note wobble-base pair with TNFa-targeting strand).

```
HCV    5' G   G    CUCCACCAUGAAUC               A 3'
         GC ACA              ACUCCCCUGUGAGG      (SEQ ID NO: 56)
         CG UGU              UGAGGGGACACUCC
Guide#1 3'                                  5' (SEQ ID NO: 54)
mfe: -34.7 kcal/mol
TNFa   5' G      UGCUCCC              C 3'
          CCUC       CAGGGGAGUUGUGU              (SEQ ID NO: 51)
          GGAG       GUCCCCUCAACACG
Guide#2 3'     U                     5'          (SEQ ID NO: 55)
mfe: -35.3 kcal/mol
```

It will be appreciated by one skilled in the art that synthetic multitargeting interfering RNA duplexes will comprise the seed and its corresponding complement (5' CAGGGGAGU 3'). (SEQ ID NO: 46)

If required, overhangs can be added. It may be beneficial to make those complementary to the intended target so as to enhanced improved binding of the tail region. The added bases may be selected so as to provide predicted binding to a specified further region in the target RNA. For example, in the Other seeds perhaps worthy of further investigation are 5' CGCCTGGAGCCCT 3' (SEQ ID NO: 61) and 5' CTC-CTCGGCCAGC 3'. (SEQ ID NO: 62)

It will be appreciated by one skilled in the art that synthetic multitargeting interfering RNA duplexes will comprise the seed and its corresponding complement:

```
(5' AGGGCUCCAGGCG 3'  (SEQ ID NO: 63) or
5' GCUGGCCGAGGAG 3'). (SEQ ID NO: 64)
```

EXAMPLE 5

Modifications to Improve Strand Loading

A likely explanation for the decreased activity of blunt-ended CODEMIRs is that RISC loading is impaired in the absence of 3' overhangs. We have investigated the use of a single blunt-end to prevent loading of one strand of a CODEMIR; a technique that is potentially useful for promoting loading of the guide strand. For this study, we designed a variant of CODEMIR-17, which has a strong preference for loading of the ICAM targeting guide strand. The variant CODEMIR-103 (Table 5-1) was designed to include a blunt-end at the 5' end of the ICAM-1 guide strand. This CODEMIR demonstrated increased VEGF suppressive activity, and decreased ICAM-1 suppressive activity (FIG. 3), which is consistent with altered strand loading.

Figure 3:
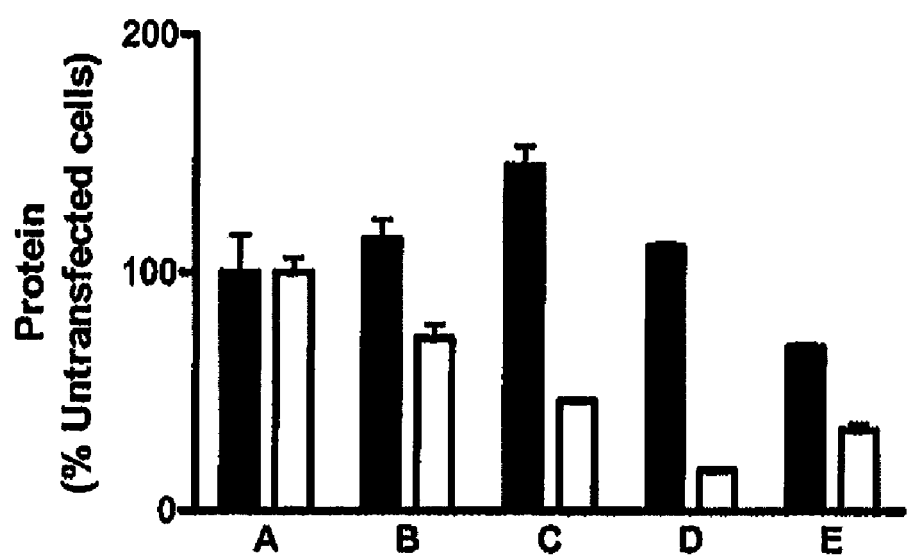
FIG. 3. Effect of a single blunt-end on VEGF and ICAM suppressive activity of CODEMIR targeting these two proteins. A: untransfected cells; B: mock transfected; C: Irrelevant control siRNA; D: CODEMIR-17 and E: CODEMIR-103. ARPE-19 cells were transfected with 40 nM duplex RNA and VEGF (closed bars) or ICAM (open bars) expression was assayed 48 hours post-transfection. Each bar represents the mean of triplicate samples. Error bars indicate standard deviation of the mean.

In this example, ARPE-19 cells were transfected with 40 nM duplex RNA and VEGF (ELISA) or ICAM (FACS) expression was assayed 48 hours post-transfection. Each bar in FIG. 3 represents the mean of triplicate samples. Error bars indicate standard deviation of the mean.

controls plus a number of multitargeting interfering RNA. One could also consider including siRNA to VEGF as known comparators.

In this model, beginning on Day 1 of life, litters are exposed to cycles of hyperoxia followed by several days of room air. The injections could be performed on the last day of cycling, prior to the 4 day normoxia period. Several days later, animals could be injected with FITC-dextran and sacrificed. Fluorescence images of the retinal flat mounts could used to estimate the extent of neoangiogenesis in each animal. In addition, measurement of the production of the target RNA molecules or their encoded proteins (in this case, VEGF and ICAM) could be made by analysis of homogenized samples or, alternatively, with in situ hybridization.

As a further non-limiting example, CODEMIRs could alternatively be evaluated in vivo for inhibition of disease-related angiogenesis using the laser-induced Choroidal Neovascularization (CNV) model in rats or primates. In this model, animals under general anaesthesia have their pupils dilated and retina photographed. Choroidal neovascularisation (CNV) is induced by krypton laser photocoagulation. This is performed using laser irradiation to either the left or alternatively, the right eye of each animal from all treatment groups through a slit lamp. A total of 6-11 laser burns are generally applied to each eye surrounding the optic nerve at the posterior pole.

At a suitable time following laser injury, the multitargeting interfering RNA are injected into the affected eyes. The suitable time can be the day following laser induction, or for an assessment against established CNV, the injections can be

TABLE 5-1

Sequences of CODEMIR-17 and its single-blunt-ended variant CODEMIR-103.

| | Duplex (top strand 5' to 3'; bottom strand 3' to 5') | | mRNA binding (RNA hybrid) | |
|---|---|---|---|---|
| CODEMIR-17 | ICAM Guide | | VEGF | |
| | UCGAGUGACAGUCACUAGCUC | (SEQ ID NO: 7) | 5' UGAUCG GUGACAGUCACUAGCU 3' | (SEQ ID NO: 9) |
| | CUAGCUCACUGUCAGUGAUCG | (SEQ ID NO: 8) | 3' CUAGCU CACUGUCAGUGAUCG 5' | (SEQ ID NO: 8) |
| | VEGF Guide | | ICAM | |
| | | | 5' GGGGAAUCAGUGACUGUCACUCGAG 3' | (SEQ ID NO: 10) |
| | | | 3' CUCGA UCACUGACAGUGAGCU 5' | (SEQ ID NO: 7) |
| CODEMIR-103 | ICAM Guide | | VEGF | |
| | GAUCGAGUGACAGUCACUAGCUC | (SEQ ID NO: 65) | 5' UGAUCG GUGACAGUCACUAGCU 3' | (SEQ ID NO: 9) |
| | CUAGCUCACUGUCAGUGAUCG | (SEQ ID NO: 8) | 3' CUAGCUCACUGUCAGUGAUCG 5' | (SEQ ID NO: 8) |
| | VEGF Guide | | ICAM | |
| | | | 5' GGGGAAUCAGUGACUGUCACUCGAGA 3' | (SEQ ID NO: 66) |
| | | | 3' CUCGA UCACUGACAGUGAGCUAG 5' | (SEQ ID NO: 65) |

EXAMPLE 6

Activity of CODEMIRs and VIROMIRs In Vivo

The activity of CODEMIRs and other multitargeting interfering RNA of the invention could be tested in various pre-clinical models known to those skilled in the art. As a non-limiting example, CODEMIRs-26-28 could be tested in a retinopathy of prematurity model. This model is well known to those working in the field of ocular angiogenesis and is used extensively as one of several models for the development of drugs active against the diseases of interest (AMD, diabetic retinopathy etc). The study could comprise of a suitable number of mouse or rat neonate pups equally divided into treatment groups. The treatment groups could include negative controls such as vehicle, irrelevant or scrambled sequence performed several days or weeks following injury. Intravitreal injections of the oligonucleotides are performed by inserting a 30- or 32-gauge needle into the vitreous. Insertion and infusion can be performed and directly viewed through an operating microscope. Care is taken not to injure the lens or the retina. Ideally, the test compounds are placed in the superior and peripheral vitreous cavity. Periodically after treatment, the neoangiogenesis is evaluated by either imaging and/or direct sampling (eg histology, immunohistochemistry). In all cases, the assessment of CNV is best performed by a skilled operator blinded to the actual treatment to ensure a lack of bias in the recording of the information.

An example of a direct imaging method is Colour Fundus Photography (CFP). Again, under anaesthesia as described above, the pupils are dilated. The fundus is then photographed with a camera using the appropriate film.

Alternatively, or preferably in addition to CFP, fluorescein angiography is used to image the vessels and areas of vascular leakage in the retina. This is performed on all of the animals following the intraperitoneal or intravenous injection of sodium fluorescein. The retinal vasculature is then photographed using the same camera as used for CFP but with a barrier filter for fluorescein angiography added. Single photographs can be taken at 0.5-1 minute intervals immediately after the administration of sodium fluorescein. The extent of fluorescein leakage is scored by a trained operator. The mean severity scores from each of the time points are compared by a suitable statistical analysis and differences considered significant at p<0.05. In addition, the frequency of each lesion score is counted, tabulated and represented graphically.

Alternatively, or in addition, rats can be euthanised at selected time points following treatment (for example 7, 14 and 28 days post injection) and eyes examined by conventional histopathology. A reduction in the number and severity of lesions is expected to be seen with samples treated by active oligonucleotides of the invention.

Other non-limiting examples including testing the multi-targeting interfering RNA of the invention in other preclinical models such as those that are well known to those skilled in the art. A non-exhaustive list includes pulmonary fibrosis (bleomycin induced), paw inflammation (carrageen), joint arthritis, diabetes, viral infection, tumour xenografts etc.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All references are hereby incorporated into this application in their entirety.

What is claimed is:

1. A method for making a multitargeting interfering RNA molecule, comprising the steps of:
 a) selecting one or more target RNA molecules, wherein the modulation in expression of the target RNA molecules is desired;
 b) obtaining at least one nucleotide sequence for each of the target RNA molecules;
 c) selecting a length, n, in nucleotides, for a seed sequence, wherein n=about 6 or more;
 d) obtaining a collection of candidate seed sequences of the length n from each nucleotide sequence obtained in step b), wherein a candidate seed sequence and its complete complement are not palindromic, and the candidate seed sequence occurs at least once in one or more of the nucleotide sequences obtained in step b), and its complete complement occurs at least once in one or more of the nucleotide sequences obtained in step b);
 e) determining the genetic context of each of the candidate seed sequence and its complete complement, by collecting, for each occurrence of the candidate seed sequence and its complete complement, 5' and 3' flanking sequence of each of the candidate seed sequences;
 f) selecting a seed sequence of the length n from the collection of candidate seed sequences obtained in step d);
 g) selecting a first consensus target sequence, which comprises the seed sequence selected in step f) and a consensus 3'-flanking sequence to a seed sequence determined from the sequences obtained in step b);
 h) selecting a second consensus target sequence, which comprises the complete complement of the seed sequence and a consensus 3'-flanking sequence to the complete complement of the seed sequence determined from the sequences obtained in step b);
 i) obtaining a first strand sequence, which comprises the first consensus target sequence selected in step g) and, adjacent to and connected with the 5'-end of the first consensus target sequence, a complement of the consensus 3' flanking sequence of step h);
 j) obtaining a second strand sequence which comprises the second consensus target sequence selected in step h)

and, adjacent to and connected with the 5'-end of the second consensus target sequence, a complement of the consensus 3' flanking sequence of step g), and;

k) making a multitargeting interfering RNA molecule comprising a first strand having the first strand sequence in step i) and a second strand having the second strand sequence obtained in step j), wherein the multitargeting interfering RNA molecule targets VEGF-A.

2. The method of claim 1 wherein the step of obtaining a collection of candidate seed sequences of the length n comprises the steps of:
   i) generating a first collection of sequences of the length n from each of the nucleotide sequences obtained in step b) of claim 1, using a method comprising the steps of:
      1) beginning at a terminus of a nucleotide sequence obtained in step b) of claim 1;
      2) sequentially observing the nucleotide sequence using a window size of n; and
      3) stepping along the nucleotide sequence with a step size of 1 nucleotide;
   ii) generating a second collection of sequences each of which is completely complementary to a sequence in the first collection; and
   iii) obtaining the collection of candidate seed sequences of the length n from the inspection of the first and the second collections of sequences generated in step i, wherein a candidate seed sequence and its complete complement are not palindromic, and each candidate seed sequence and its complete complement occurs at least once in the nucleotide sequences obtained in step b) of claim 1.

3. The method of claim 1 wherein the step of obtaining a collection of candidate seed sequences of the length n comprises the steps of:
   i) obtaining the completely complementary sequence for each nucleotide sequence obtained in step (b) of claim 1;
   ii) generating a first collection of sequences of the length n from each of the nucleotide sequences obtained in step b) of claim 1 and a second collection of sequences of the length n from each of the completely complementary sequences obtained in step (i), using a method comprising the steps of:
      1) beginning at a terminus of the nucleotide sequence of each of the nucleotide sequences obtained in step b) of claim 1 or each of the completely complementary sequences obtained in step (i);
      2) sequentially observing the nucleotide sequence using a window size of n; and
      3) stepping along the nucleotide sequence with a step size of 1 nucleotide; and
   iii) obtaining the collection of candidate seed sequences of the length n by the inspection of the first and the second collections of sequences generated in step ii, wherein a candidate seed sequence and its complete complement are not palindromic, and each of the candidate seed sequences is present in both the first and the second collections of sequences.

4. The method of claim 1, wherein the step of selecting a group of candidate seed sequences as recited in claim 1 comprises the step of discarding any sequence of the length n that
   i) is composed of a consecutive string of 5 or more identical single nucleotides;
   ii) is composed of only adenosine and uracil;
   iii) is any combination of i) to iv); or
   iv) is palindromic.

5. The method of claim 1, wherein each of the steps of selecting a first and a second consensus target sequence comprises the step of discarding any sequence that
   i) is composed of only a single base;
   ii) is composed of only adenosine and uracil;
   iii) has a consecutive string of five or more bases which are cytosine; or
   iv) is any combination of i) to iii).

6. The method of claim 1, further comprising the step of modifying the multitargeting interfering RNA molecule,
   i) to improve the incorporation of the first and the second strands of the multitargeting interfering RNA molecule into the RNA induced silencing complex (RISC);
   ii) to increase or decrease the modulation of the expression of at least one target RNA molecule;
   iii) to decrease stress or inflammatory response when the multitargeting interfering RNA molecule is administered into a subject;
   iv) to alter half life in an expression system; or
   v) any combination of i) to iv).

7. The method of claim 1, further comprising repeating the steps c) to k) of claim 1 with a new value of n.

8. The method of claim 1, further comprising the steps of testing the multitargeting interfering RNA molecule in an expression system.

9. The method of claim 1, wherein in the step of selecting a first consensus target sequence, the consensus 3' flanking sequence to the seed sequence comprises a sequence that is at least partially identical to the 3' flanking sequence to the seed sequence in at least one sequence obtained in step b) of claim 1.

10. The method of claim 9, wherein the consensus 3'-flanking sequence to the seed sequence comprises a sequence that is identical to the 3' flanking sequence to the seed sequence in at least one sequence obtained in step b) of claim 1.

11. The method of claim 1, wherein in the step of selecting a second consensus target sequence, the consensus 3' flanking sequence to the complete complement of the seed sequence comprises a sequence that is at least partially identical to the 3' flanking sequence to the complete complement of the seed sequence in at least one sequence obtained in step b) of claim 1.

12. The method of claim 1, wherein the consensus 3' flanking sequence to the complete complement of the seed sequence comprises a sequence that is identical to the 3'-flanking sequence to the seed sequence in the sequences obtained in step b) of claim 1.

13. The method of claim 1, wherein in the step of obtaining a first strand sequence, the complement of the consensus 3' flanking sequence is a complete complement of the consensus 3' flanking sequence of step h) of claim 1.

14. The method of claim 1, wherein in the step of obtaining a second strand sequence, the complement of the consensus 3' flanking sequence is a complete complement of the consensus 3' flanking sequence of step g) of claim 1.

15. The method of claim 1, wherein in the step of making a multitargeting interfering RNA molecule, the first strand and the second strand are completely complementary to each other, excepting the overhangs if present.

16. The method of claim 1, wherein in the step of making a multitargeting interfering RNA molecule, the first strand and the second strand are incompletely complementary to each other.

* * * * *

```
SEQUENCE LISTING

<160> NUMBER OF SEQ ID NOS: 75

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agtgactgtc ac                                                         12

<210> SEQ ID NO 2
<211> LENGTH: 12
<212> TYPE: RNA
<213> ORGANISM: Artificial Sequence
<220> FEATURE:
<223> OTHER INFORMATION: Description of Artificial Sequence: Synthetic
      complementary oligonucleotide

<400> SEQUENCE: 2
gugacaguca cu                                                         12

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      ICAM guide oligonucleotide

<400> SEQUENCE: 3
cgagugacag ucacuagcuc c                                               21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      VEGF guide oligonucleotide

<400> SEQUENCE: 4
agcuagugac ugucacucga u                                               21

<210> SEQ ID NO 5
```

```
<211> LENGTH: 22
<212> TYPE: RNA
<213> ORGANISM: Artificial Sequence
<220> FEATURE:
<223> OTHER INFORMATION: Description of Artificial Sequence: Synthetic
      VEGF binding oligonucleotide

<400> SEQUENCE: 5
gaucggugac agucacuagc uu                                                 22

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      ICAM binding oligonucleotide

<400> SEQUENCE: 6
cggggaauca gugacuguca cucga                                              25

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      ICAM guide oligonucleotide

<400> SEQUENCE: 7
ucgagugaca gucacuagcu c                                                  21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      VEGF guide oligonucleotide

<400> SEQUENCE: 8
gcuagugacu gucacucgau c                                                  21

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      VEGF binding oligonucleotide

<400> SEQUENCE: 9
ugaucgguga cagucacuag cu                                                 22

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      ICAM binding oligonucleotide

<400> SEQUENCE: 10
ggggaaucag ugacugucac ucgag                                              25

<210> SEQ ID NO 11
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      ICAM guide oligonucleotide

<400> SEQUENCE: 11
ucgagugaca gucacuagcu cc                                              22

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      VEGF binding oligonucleotide

<400> SEQUENCE: 12
agcuagugac ugucacucga uc                                              22

<210> SEQ ID NO 13
<211> LENGTH: 26
<212> TYPE: RNA
<213> ORGANISM: Artificial Sequence
<220> FEATURE:
<223> OTHER INFORMATION: Description of Artificial Sequence: Synthetic
      ICAM binding oligonucleotide

<400> SEQUENCE: 13
cggggaauca gugacuguca cucgag                                          26

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      VEGF guide oligonucleotide

<400> SEQUENCE: 14
agcuagugac ugucacuuga u                                               21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      ICAM guide oligonucleotide

<400> SEQUENCE: 15
ucgagugaca gucacuaguu c                                               21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      ICAM guide oligonucleotide

<400> SEQUENCE: 16
cgagugacag ucacugauuc c                                               21

<210> SEQ ID NO 17
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      VEGF guide oligonucleotide

<400> SEQUENCE: 17
agcuagugac ugucaccgau c                                                 21

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      ICAM binding oligonucleotide

<400> SEQUENCE: 18
gggaaucagu gacugucacu cga                                               23

<210> SEQ ID NO 19
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide in glucose-6-phosphatase and Inpp11

<400> SEQUENCE: 19
cugccucgcc cag                                                          13

<210> SEQ ID NO 20
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide in glucose-6-phosphatase and Inpp11

<400> SEQUENCE: 20
cuccacaucc ac                                                           12

<210> SEQ ID NO 21
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide complementary to SEQ ID NO: 19

<400> SEQUENCE: 21
cugggcgagg cag                                                          13

<210> SEQ ID NO 22
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide complementary to SEQ ID NO: 20

<400> SEQUENCE: 22
guggaugugg ag                                                           12

<210> SEQ ID NO 23
<211> LENGTH: 39
<212> TYPE: RNA
<213> ORGANISM: Artificial Sequence
<220> FEATURE:
<223> OTHER INFORMATION: Description of Artificial Sequence: Synthetic
      Gluc6p oligonucleotide
```

```
<400> SEQUENCE: 23
gugucauccc cuacugccuc gcccaggucc ugggccagc                                  39

<210> SEQ ID NO 24
<211> LENGTH: 39
<212> TYPE: RNA
<213> ORGANISM: Artificial Sequence
<220> FEATURE:
<223> OTHER INFORMATION: Description of Artificial Sequence: Synthetic
      Inpp11 complement oligonucleotide

<400> SEQUENCE: 24
caggcacuca ugccugccuc gcccagcccg cuggcccgc                                  39

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      Inpp11 targeting strand oligonucleotide

<400> SEQUENCE: 25
augccugccu cgcccagguc c                                                     21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      Gluc6p targeting strand oligonucleotide

<400> SEQUENCE: 26
ggaccugggc gaggcaggca u                                                     21

<210> SEQ ID NO 27
<211> LENGTH: 41
<212> TYPE: RNA
<213> ORGANISM: Artificial Sequence
<220> FEATURE:
<223> OTHER INFORMATION: Description of Artificial Sequence: Synthetic
      Gluc6p oligonucleotide

<400> SEQUENCE: 27
gauucuucca cuggcuccac auccacccca cuggaucuuc a                               41

<210> SEQ ID NO 28
<211> LENGTH: 41
<212> TYPE: RNA
<213> ORGANISM: Artificial Sequence
<220> FEATURE:
<223> OTHER INFORMATION: Description of Artificial Sequence: Synthetic
      Inpp11 complement oligonucleotide

<400> SEQUENCE: 28
accagccgcc cacccuccac auccacgcuc agcgugaacu u                               41

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      Inpp11 targeting strand oligonucleotide

<400> SEQUENCE: 29
```

```
cacccuccac auccacccca c                                              21
```

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      Gluc6p targeting strand oligonucleotide

<400> SEQUENCE: 30

```
guggggugga uguggagggu g                                              21
```

<210> SEQ ID NO 31
<211> LENGTH: 83
<212> TYPE: DNA
<213> ORGANISM: Artificial Sequence
<220> FEATURE:
<223> OTHER INFORMATION: Description of Artificial Sequence: Synthetic
      HIV seed oligonucleotide

<400> SEQUENCE: 31

```
tctaattcca ataattcttg ttcattcttt tcttgctggt tttgcgattc ttcaattaag    60
gagtgtatta agcttgtgta att                                           83
```

<210> SEQ ID NO 32
<211> LENGTH: 83
<212> TYPE: DNA
<213> ORGANISM: Artificial Sequence
<220> FEATURE:
<223> OTHER INFORMATION: Description of Artificial Sequence: Synthetic
      HIV complementary oligonucleotide

<400> SEQUENCE: 32

```
ctttgagcca attcccatac attattgtgc cccggctggt tttgcgattc taaaatgtaa    60
taataagacg ttcaatggaa cag                                           83
```

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      HIV seed sequence

<400> SEQUENCE: 33

```
gctggttttg cgattct                                                   17
```

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      HIV seed complementary sequence

<400> SEQUENCE: 34

```
agaatcgcaa aaccagc                                                   17
```

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      modified seed sequence -continued

<400> SEQUENCE: 35
tggttttgcg attct                                              15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      modified complementary sequence

<400> SEQUENCE: 36
agaatcgcaa aacca                                              15

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      viromir duplex sequence

<400> SEQUENCE: 37
ugcugguuuu gcgauucuaa a                                       21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      viromir targeting sequence

<400> SEQUENCE: 38
uagaaucgca aaccagcaa g                                        21

<210> SEQ ID NO 39
<211> LENGTH: 66
<212> TYPE: DNA
<213> ORGANISM: Artificial Sequence
<220> FEATURE:
<223> OTHER INFORMATION: Description of Artificial Sequence: Synthetic
      shRNA viromir oligonucleotide

<400> SEQUENCE: 39
gatccgcttg ctggttttgc gattctaact cgagatagaa tcgcaaaacc agcaagtttt    60
ttggaa                                                              66

<210> SEQ ID NO 40
<211> LENGTH: 66
<212> TYPE: DNA
<213> ORGANISM: Artificial Sequence
<220> FEATURE:
<223> OTHER INFORMATION: Description of Artificial Sequence: Synthetic
      shRNA complementary strand oligonucleotide

<400> SEQUENCE: 40
agctttccaa aaaacttgct ggttttgcga ttctatctcg agttagaatc gcaaaaccag    60
caagcg                                                              66

<210> SEQ ID NO 41
<211> LENGTH: 9
<212> TYPE: DNA
<213> ORGANISM: Artificial Sequence
<220> FEATURE:

<223> OTHER INFORMATION: Description of Artificial Sequence: Synthetic
      seed sequence in HCV and TNFalpha

<400> SEQUENCE: 41 actccctg                                                                9

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      extended seed sequence

<400> SEQUENCE: 42 actccctgt gagga                                                         15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      extended seed sequence

<400> SEQUENCE: 43 actccctga cgccg                                                         15

<210> SEQ ID NO 44
<211> LENGTH: 66
<212> TYPE: DNA
<213> ORGANISM: Artificial Sequence
<220> FEATURE:
<223> OTHER INFORMATION: Description of Artificial Sequence: Synthetic
      HCV with seed sequence

<400> SEQUENCE: 44 tgatggggc gacactccac catgaatcac tccctgtga ggaactactg tcttcacgca         60
gaaagc                                                                  66

<210> SEQ ID NO 45
<211> LENGTH: 66
<212> TYPE: DNA
<213> ORGANISM: Artificial Sequence
<220> FEATURE:
<223> OTHER INFORMATION: Description of Artificial Sequence: Synthetic
      TNFalpha seed sequence

<400> SEQUENCE: 45
gacagtgagt aacgactcgg agacgagggg tccctcaac acagacatta gcgggatgat        60
aagtca                                                                  66

<210> SEQ ID NO 46
<211> LENGTH: 9
<212> TYPE: RNA
<213> ORGANISM: Artificial Sequence
<220> FEATURE:
<223> OTHER INFORMATION: Description of Artificial Sequence: Synthetic
      HCV seed sequence

<400> SEQUENCE: 46 cagggagu                                                                9

<210> SEQ ID NO 47
<211> LENGTH: 14
<212> TYPE: RNA

-continued

<213> ORGANISM: Artificial Sequence
<220> FEATURE:
<223> OTHER INFORMATION: Description of Artificial Sequence: Synthetic
HCV seed sequence

<400> SEQUENCE: 47
ccucacaggg gagu 14

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
TNFalpha sequence

<400> SEQUENCE: 48
ccucacaggg gaguugugu 19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
TNFalpha complement sequence

<400> SEQUENCE: 49
acacaacucc ccugugagg 19

<210> SEQ ID NO 50
<211> LENGTH: 33
<212> TYPE: RNA
<213> ORGANISM: Artificial Sequence
<220> FEATURE:
<223> OTHER INFORMATION: Description of Artificial Sequence: Synthetic
guide strand sequence

<400> SEQUENCE: 50
gacacuccac caugaaucac uccccuguga gga 33

<210> SEQ ID NO 51
<211> LENGTH: 27
<212> TYPE: RNA
<213> ORGANISM: Artificial Sequence
<220> FEATURE:
<223> OTHER INFORMATION: Description of Artificial Sequence: Synthetic
TNFalpha guide sequence

<400> SEQUENCE: 51
gccucugcuc cccaggggag uuguguc 27

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
HCV extension sequence

<400> SEQUENCE: 52
uccucacagg ggaguugugu 20

<210> SEQ ID NO 53
<211> LENGTH: 20
<212> TYPE: RNA
<213> ORGANISM: Artificial Sequence
<220> FEATURE:

```
<223> OTHER INFORMATION: Description of Artificial Sequence: Synthetic
      HCV guide sequence

<400> SEQUENCE: 53
aggagugucc ccucaacaca                                                    20

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      alternative TNFalpha sequence

<400> SEQUENCE: 54
ccucacaggg gaguugugc                                                     19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      alternative TNFalpha complementary strand sequence

<400> SEQUENCE: 55
gcacaacucc ccugugagg                                                     19

<210> SEQ ID NO 56
<211> LENGTH: 36
<212> TYPE: RNA
<213> ORGANISM: Artificial Sequence
<220> FEATURE:
<223> OTHER INFORMATION: Description of Artificial Sequence: Synthetic
      HCV strand sequence

<400> SEQUENCE: 56
ggcgacacuc caccaugaau cacuccccug ugagga                                  36

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      HCV sequence

<400> SEQUENCE: 57
ccucacaggg gaguugugcc c                                                  21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      HCV complementary strand sequence

<400> SEQUENCE: 58
gcacaacucc ccugugaggc u                                                  21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      extended sequence of SEQ ID NO: 57
```

```
<400> SEQUENCE: 59
ccucacaggg gaguugugcu u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      extended SEQ ID NO: 58 sequence

<400> SEQUENCE: 60
gcacaacucc ccugugaggu u                                              21

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Synthetic
      alternative seed sequence

<400> SEQUENCE: 61
cgcctggagc cct                                                       13

<210> SEQ ID NO 62
<211> LENGTH: 13
<212> TYPE: DNA
<213> ORGANISM: Artificial Sequence
<220> FEATURE:
<223> OTHER INFORMATION: Description of Artificial Sequence: Synthetic
      alternative seed sequence

<400> SEQUENCE: 62
ctcctcggcc agc                                                       13

<210> SEQ ID NO 63
<211> LENGTH: 13
<212> TYPE: RNA
<213> ORGANISM: Artificial Sequence
<220> FEATURE:
<223> OTHER INFORMATION: Description of Artificial Sequence: Synthetic
      seed of multitargeting interfering RNA duplex

<400> SEQUENCE: 63
agggcuccag gcg                                                       13

<210> SEQ ID NO 64
<211> LENGTH: 13
<212> TYPE: RNA
<213> ORGANISM: Artificial Sequence
<220> FEATURE:
<223> OTHER INFORMATION: Description of Artificial Sequence: Synthetic
      seed of synthetic multitargeting interfering RNA duplex
      complement

<400> SEQUENCE: 64
gcuggccgag gag                                                       13

<210> SEQ ID NO 65
<211> LENGTH: 23
<212> TYPE: RNA
<213> ORGANISM: Artificial Sequence
<220> FEATURE:
<223> OTHER INFORMATION: Description of Artificial Sequence: Synthetic
      ICAM mRNA binding (RNA hybrid)
```

-continued

```
<400> SEQUENCE: 65
gaucgaguga cagucacuag cuc                                            23

<210> SEQ ID NO 66
<211> LENGTH: 26
<212> TYPE: RNA
<213> ORGANISM: Artificial Sequence
<220> FEATURE:
<223> OTHER INFORMATION: Description of Artificial Sequence: Synthetic
      ICAM mRNA binding sequence

<400> SEQUENCE: 66
ggggaaucag ugacugucac ucgaga                                         26

<210> SEQ ID NO 67
<211> LENGTH: 23
<212> TYPE: RNA
<213> ORGANISM: Artificial Sequence
<220> FEATURE:
<223> OTHER INFORMATION: Description of Artificial Sequence: Synthetic
      VEGF binding sequence

<400> SEQUENCE: 67
ugaucgguga cagucacuag cuu                                            23

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctgagaatcg                                                           10

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cgaaagtcag                                                           10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cgattgtcag                                                           10

<210> SEQ ID NO 71
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
```

-continued

```
cacccuccac auccacccca cag                                    23

<210> SEQ ID NO 72
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
guggggugga uguggagggu ggu                                    23

<210> SEQ ID NO 73
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aaguucacgc uggcugagcg uggaugugga gggugggcgg cuggu            45

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
cacccuccac auccacgcua cag                                    23

<210> SEQ ID NO 75
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
guggggugga uguggaggca ggu                                    23
```